United States Patent [19]
Hostetler

[11] Patent Number: 5,879,700
[45] Date of Patent: Mar. 9, 1999

[54] NUCLEOSIDE ANALOGUE PHOSPHATES FOR TOPICAL USE

[76] Inventor: Karl Y. Hostetler, 14024 Rue St. Raphael, Del Mar, Calif. 92014

[21] Appl. No.: 480,456

[22] Filed: Jun. 7, 1995

Related U.S. Application Data

[63] Continuation-in-part of Ser. No. 60,258, May 12, 1993, Pat. No. 5,580,571, which is a continuation-in-part of Ser. No. 777,683, Oct. 15, 1991, abandoned.

[51] Int. Cl.$^6$ ........................................................ A61K 9/70
[52] U.S. Cl. ............................................ 424/443; 558/166
[58] Field of Search ............................. 424/443; 558/166

[56] References Cited

U.S. PATENT DOCUMENTS

| | | |
|---|---|---|
| 3,457,253 | 7/1969 | Wechter . |
| 4,146,715 | 3/1979 | Schaeffer . |
| 4,199,574 | 4/1980 | Schaeffer . |
| 4,294,831 | 10/1981 | Schaeffer . |
| 4,323,573 | 4/1982 | Schaeffer . |
| 4,360,522 | 11/1982 | Schaeffer . |
| 4,634,719 | 1/1987 | Takaishi et al. . |
| 4,758,572 | 7/1988 | Spector et al. . |
| 4,897,394 | 1/1990 | Zimmerman et al. . |
| 5,021,437 | 6/1991 | Blumenkopf . |
| 5,223,263 | 6/1993 | Hostetler et al. . |
| 5,274,162 | 12/1993 | Glazier ................................. 558/166 |

FOREIGN PATENT DOCUMENTS

| | | |
|---|---|---|
| 0095813 | 12/1983 | European Pat. Off. . |
| 0121635 | 10/1984 | European Pat. Off. . |
| 0165164 | 12/1985 | European Pat. Off. . |
| 0350287 | 7/1989 | European Pat. Off. . |
| 0381533 | 8/1990 | European Pat. Off. . |
| 3543346 | 6/1986 | Germany . |
| 1590500 | 6/1981 | United Kingdom . |
| 2168350 | 6/1986 | United Kingdom . |
| WO 91/19721 | 12/1991 | WIPO . |
| WO91/19721 | 12/1991 | WIPO . |

OTHER PUBLICATIONS

Glazier, A., "The Metabolism and Antiviral Activity of a Novel Group of Anti–Herpes Prodrugs", pp. 1–25.

Darby, G. (1980) Sensitivity of Viruses to Phosphorylated 9–(2–hydroxyethoxymethyl) guanine Revealed in TK–transformed Cells. J. Gen. Virol. 48:451–454.

Prisbe, E.J. et al. (1986) Synthesis and Antiherpes Virus Activity of Phosphate and Phosphonate Derivatives of 9–[(1,3–Dihydroxy–2–propoxy)methyl] guanine. J. Med. Chem. 29:671–675.

Glazier, A. et al. The metabolism and antiviral activity of a novel group of anti–herpes prodrugs. Paper No. 90, presented at The Ninth International Conference on Antiviral Research. Uribandai, Fukushima, Japan, May 23, 1996.

Agranoff, B. et al. (1963) Cytidine Diphosphatase–dl–Dipalmitin. Biochem. Prep. 10:47–51.

Ellis, M. et al. (1989) Orofacial infection of athymic mice with defined mixtures of acyclovir–susceptible and acyclovir–resistant herpes simplex virus type 1. Antimicrobial Agents and Chemotherapy 33(3):304–310.

Furman, P. et al. (1979) Inhibition of herpes simplex virus–induced DNA polymerase activity and viral DNA replication by 9–(2–hydroxyethoxymethyl)guanine and its triphosphate. J. Virol. 32:72–77.

(List continued on next page.)

*Primary Examiner*—Carlos A. Azpuru
*Attorney, Agent, or Firm*—Knobbe, Martens, Olson & Bear, LLP

[57] ABSTRACT

Compositions for topical use in herpes virus infections comprising anti-herpes nucleoside analogue phosphate esters, such as acyclovir monophosphate, acyclovir diphosphate, and acyclovir triphosphate which show increased activity against native strains of herpes virus as well as against resistant strains, particularly thymidine kinase negative strains of virus. Also disclosed are methods for treatment of herpes infections with nucleoside phosphates. Anti-herpes nucleoside analogues phosphate esters include the phosphoramidates and phosphothiorates, as well as polyphosphates comprising C and S bridging atoms.

38 Claims, 3 Drawing Sheets

OTHER PUBLICATIONS

Fyfe, J. et al. (1978) Thymidine kinase from herpes simplex virus phosphorylates the new antiviral compound, 9–(2–hydroxyethoxymethyl)guanine. J. Biol. Chem. 253:8721–8727.

Gomez–almaguer, D. et al. (1988) Acyclovir in the treatment of aplastic anemia. Amer. J. of Hematology 29:172–173.

King (1988) History, pharmacokinetics, and pharmacology of acyclovir. J. Am. Acad. Dermatol. 18:176–179 (Abstract only).

Krenitsky, T. et al. (1990) Nucleotide analogue inhibitors of purine nucleoside phosphorylase. The Journal of Biological Chemistry 265(6):3066–3069.

Lobe, D. et al. (1991) Synergistic topical therapy by acyclovir and A11OU for herpes simplex virus induced zosteriform rash in mice. Antiviral Research 15:87–100.

Masch et al. (1965) Nivea, the Prototype of Lanolin Absorption Creams. A history of Nivea Cream. American Perfumer and Cosmetics 80:35–38.

Merta et al. (1990) Inhibition of herpes simplex virus DNA polymerase by diphosphates of acyclic phosphonylmethoxyalkyl nucleotide analogues. Antiviral Research 13:209–218.

O'Brien, W. et al. (1990) Nucleoside metabolism in herpes simplex virus–infected cells following treatment with interferon and acyclovir, a possible mechanism of synergistic antiviral activity. Antimicrob. Agents and Chemother. 34(6):1178–1182.

Ott, D.G. et al. (1967) Chemical synthesis of nucleoside triphosphates. Anal. Biochem. 21:469–472.

Remington's Pharmaceutical Sciences, 15th Edition., 175. Mack Publishing Company., Easton, Pennsylvania 18042. (Chapter 87: Blaug, Seymour).

Rune, S.J. et al. (1990) Acyclovir in the prevention of duodenal ulcer recurrence. Gut 31:151–152.

Spruance, S. et al. (1982) Treatment of herpes simplex labialis with topical acyclovir in polyethylene glycol. J. Infect. Dis. 146:85–90.

Spruance, S. et al. (1984) Early patient–initiated treatment of herpes labialis with topical 10% acyclovir. Antimicrob. Agents Chemother. 25:553–555.

Straus, S. (1989) Effect of oral acyclovir treatment on symptomatic and asymptomatic virus shedding in recurrent genital herpes. Sexually Transmitted Diseases 16(2):107–113.

Toorchen, D. et al. (1983) Mechanisms of chemical mutagenesis and carcinogenesis: effects of DNA replication of methylation at the 06–guanine position of dGTP. Carcinogenesis 4:1591–1597.

Welch, C.J. et al. (1985) The chemical synthesis and antiviral properties of an acyclovir–phospholipid conjugate. Acta Chemica Scandinavica B39:47–54.

Whitley, R. et al. (1990) Immunobiology and Prophylaxis of Human Herpesvirus Infections. C. Lopez (ed) Plenum Press, New York pp. 243–253.

Yoshikawa, M. et al. (1969) Phosphorylation. III. Selective phosphorylation of unprotected nucleosides. Bull. Chem. Soc. Japan 42:3505–3508.

Yoshikawa, et al. (1967) A novel method for phosphorylation of nucleosides to 5'–nucleotides. Tetrahedron Lett., 50:5065–5068.

Hoard, D., et al. (1965) Conversion of mono– and oligodeoxyribonucleotides to 5'–triphosphates[1]. J. Am. Chem. Soc. 87(8):1785–1788.

Hunt, B.J., et al. (1967) Methods, apparatus: new product research, process development and design. Chemistry and Industry 1868–1869.

Hutchinson, D.W. The synthesis, reaction and properties of nucleoside mono–, di–, tri–, and tetraphosphates and nucleotides with changes in the phosphoryl residue. In Chemistry of Nucleotides and Nucleosides, (L. Townsend, ed.) pp. 81–146 (1991).

Moffatt, J.G., et al. (1961) Nuleosides polyphosphates. XII.[1] The total synthesis of coenzyme $A^2$. J. Am. Chem. Soc. 83:663–675.

Myers, T., et al. (1963) Phosphonic acid analogs of nucleoside phosphates. I. the synthesis of 5'–adenylyl methylenediphosphonate, a phosphonic acid analog of $ATP^{1,2}$. Journal of Am. Chen. Soc. 85:3295–3295.

Seela, F., et al. (1992) 7–deazapurine containing DNA: efficiency of $c^7G_dTP$, $c^7A_dTP$ and $c^7I_dTP$ incorporation during PCR–amplification and protection from endodeoxyribonuclease hydrolysis. Nucleic Acids Research 20(1):55–61.

van Boom, J.H., et al. (1975) 2,2,2–tribromoethyl phosporomorpholinochloridate: a convenient reagent for the synthesis of . . . Tetrahedron Letters 32:2779–2782.

NUCLEOSIDE ANALOGUE PHOSPHATES FOR TOPICAL USE

RELATED APPLICATIONS

This application is a continuation-in-part of U.S. Ser. No. 08/060,258, filed May 12, 1993, now U.S. Pat. No. 5,580,571, which is a continuation-in-part of U.S. Ser. No. 07/777,683, filed Oct. 15, 1991, now abandoned.

BACKGROUND OF THE INVENTION

1. Field of the Invention

The present invention relates to the topical treatment of cutaneous virus infections. It relates particularly to the topical treatment of herpes simplex infections, including herpes simplex types 1 and 2, using formulations comprising phosphate esters of anti-herpes antiviral nucleoside analogues such as acyclovir.

2. Background of the Art

Acyclovir (ACV) is an antiviral nucleoside analogue of guanosine which contains an unusual incomplete (acyclic) sugar moiety. Nucleoside analogues interrupt the process of DNA replication in cells, and are for that reason useful as antiviral and antineoplastic agents. ACV is particularly effective in treating herpes simplex virus infections of types I and II. The antiherpes virus activity of ACV in cells occurs with low toxicity because ACV is selectively phosphorylated by HSV thymidine kinase, but not host cell thymidine kinase. As a consequence, only cells infected with HSV can form ACV monophosphate (ACV-MP). ACV-MP is then anabolically converted by cellular enzymes to ACV triphosphate, the active agent that interferes with viral replication. (Fyfe, J., et al., *J. Biol. Chem.* 253:8721–8727 (1978); Furman, P., et al., *J. Virol.* 32:72–77 (1979)).

The anti-herpes virus activity of acyclovir has been demonstrated in inhibiting the replication of herpes simplex virus in tissue culture cells (O'Brien, W., et al., *Antimicrob. Agents and Chemother.* 34:1178–1182 (1990); it has also been demonstrated in clinical studies wherein patients infected with HSV were treated with orally administered ACV (Whitley, R., *Immunobiol. and Prophylaxis of Human Herpesvirus Infections,* C. Lopez et al, (eds) Plenum Press, NY 1990; and Straus, S., *Sexually Transmitted Diseases* 16(2):107–113 (1989).

Acyclovir is the treatment of choice for mucosal and cutaneous HSV infections, although patients receiving topical acyclovir therapy experience some reductions of their symptoms, healing is slow and incomplete (Spruance, S., et al., *J. Infect. Dis.* 146:85–90 (1982); and Spruance, S., et al., *Antimicrob. Agents Chemother.* 25:553–555 (1984).

Combination treatment using ACV together with interferon for herpes virus infected cultured cells (O'Brien, W., et al., *Antimicrob. Agents and Chemother.* 34(6):1178–1182 (1990) or using ACV together with A1110U, an HSV inactivator, as a topical therapy for herpetic keratitis in athymic mice (Lobe, D., et al., *Antiviral Research* 15:87–100 (1991) showed synergistic antiherpesvirus I activity over the use of ACV alone.

Acyclovir has been used with qualified success in a clinical trial to treat another viral disease, varicella (chickenpox) (Whitley, R., et al., *Immunobiology and Prophylaxis of Human Herpesvirus Infections,* C. Lopez (ed), Plenum Press, New York (1990) pp. 243–253. It has also been used experimentally but without success in treating other disorders in which a viral etiology was hypothesized, such as aplastic anemia (Gomez-Almaguer, D., et al. *Amer. J. of Hematology* 29:172–173 (1988) and duodenal ulcer (Rune, S. J., et al., *Gut* 31:151–152 (1990)).

Acyclovir phosphates have been shown to be efficacious against wild type or laboratory isolates of HSV-1 infected cultured cells in vitro, but have little or no efficacy against thymidine kinase defective mutants of HSV under the same conditions. (See data of FIGS. 1 and 2).

In immunosuppressed patients, such as those with HIV (AIDS) infections or transplant recipients who are taking immunosuppressive drugs to prevent transplant rejection, ACV has been given chronically to prevent troublesome outbreaks of herpes. Such therapy provides a selective pressure which leads to mutations in HSV thymidine kinase (90% frequency) as well as DNA polymerase (10% frequency), which in turn results in ACV-resistant viral strains. There is no effective topical therapy for these acyclovir resistant herpes virus strains.

SUMMARY OF THE INVENTION

According to the invention, there are provided acyclovir phosphate esters and other antiherpes antiviral nucleoside analogue phosphate esters that are effective in the treatment of mucosal and cutaneous herpetic lesions due to herpes virus infections. These agents surprisingly show antiviral activity against lesions due to thymidine kinase defective herpes virus infections, even though they are relatively inactive against these mutant viruses in cultured cells. The invention also provides pharmaceutical formulations, comprising an effective, antiviral concentration of an acyclovir derivative which can be acyclovir monophosphate, acyclovir diphosphate, acyclovir triphosphate, acyclovir monophosphate glycerol, acyclovir diphosphate glycerol, acyclovir monophosphate morpholidate, acyclovir diphosphate morpholidate, acyclovir monophosphate isopropylidene glycerol, acyclovir diphosphate isopropylidene glycerol, acyclovir phosphomethylenediphosphonate, or a mixture thereof, in a pharmaceutical carrier suitable for topical use.

Other antiherpes simplex nucleosides which rely on phosphorylation by viral thymidine kinase will also exhibit enhanced activity when applied to the skin of infected patients as their phosphate esters in a suitable topical formulation.

According to another aspect of the invention, there is provided a method for the topical treatment of a viral infection, comprising applying a formulation comprising any of the acyclovir phosphate derivatives of the invention, or a mixture thereof, to the mucosal or cutaneous lesions of a virus infected animal, including a human or other mammal. In a preferred embodiment of the method, the animal is infected with a herpes virus. In a particularly preferred embodiment, the animal is infected with a herpes virus strain that is resistant to acyclovir. The acyclovir resistant herpes virus strain can be a viral strain in which resistance to the antiviral agent is due to an alteration or defect in the thymidine kinase gene.

In accordance with another aspect of the present invention, anti-herpes nucleoside analogue phosphate esters ares used in the preparation of a medicament for the treatment of a mucosal or cutaneous viral infection. In a preferred embodiment, the nucleoside phosphate is a water soluble salt. In another preferred embodiment, the viral infection is herpes simplex virus, type 1 or type 2.

In another aspect of the present invention, the anti-herpes nucleoside analogue phosphate esters are used together with a pharmaceutically acceptable carrier in the preparation of a medicament for the treatment of a mucosal or cutaneous viral infection. In a preferred respect, the pharmaceutically acceptable carrier is selected from the group consisting of an aqueous cream and polyethylene glycol.

Also provided are anti-herpes nucleoside phosphate esters such as acyclovir phosphoramidates and phosphothiorates and anti-herpes nucleoside analogue polyphosphate esters comprising sulfur and methylene bridging groups.

DETAILED DESCRIPTION OF THE INVENTION

Figure 1:
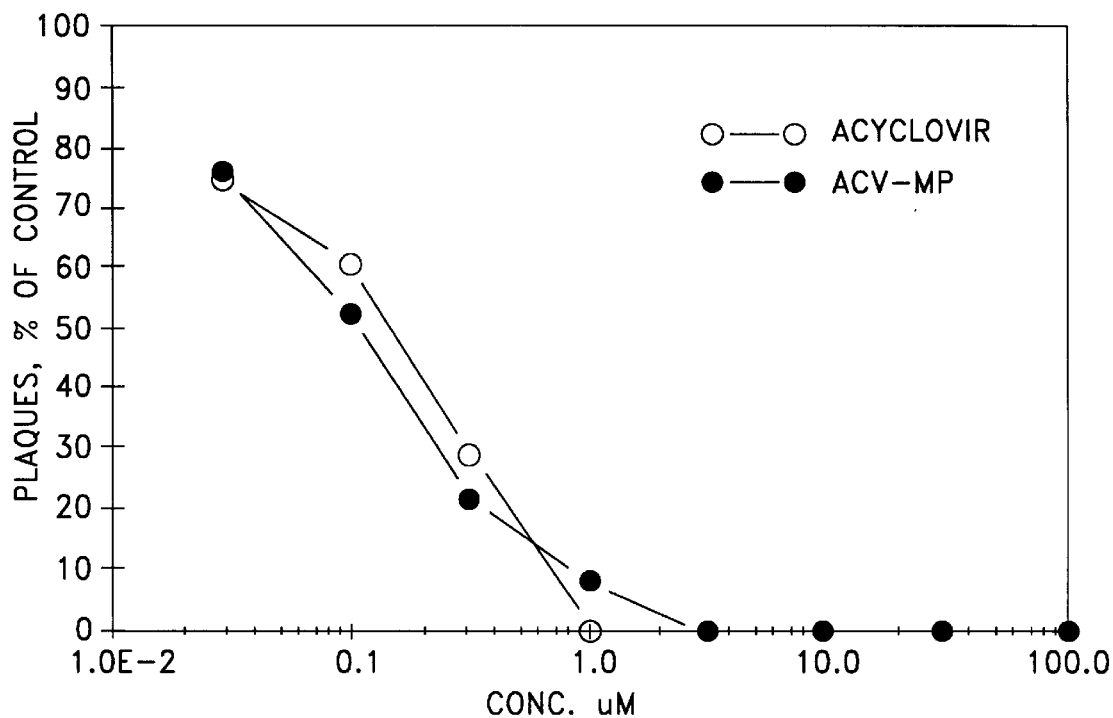
FIG. 1 illustrates the comparative effect of acyclovir and acyclovir monophosphate on herpes simplex virus replication in Wi38 fibroblasts.

The present invention provides acyclovir phosphate derivatives that demonstrate excellent topical activity against herpes simplex virus (HSV) infections, particularly against ACV-resistant mutants of HSV.

Acyclovir is an analogue of the purine base, guanine, having a substituent group at the 9-position, and having an acyclic sugar group from which the common name is derived. The chemical name of acyclovir is 9-(2-hydroxyethoxymethyl)guanine, which has the structure:

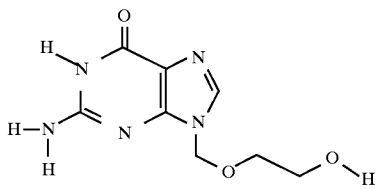

The acyclovir phosphate derivatives of the invention have a substituent, R, at the terminal O-locant of the acyclic sugar group, as follows:

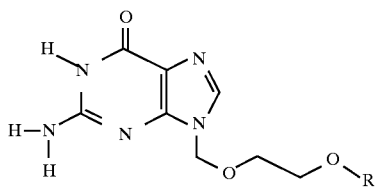

wherein the R substituents are as follows:

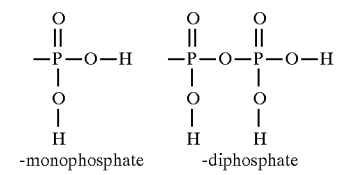
-monophosphate     -diphosphate

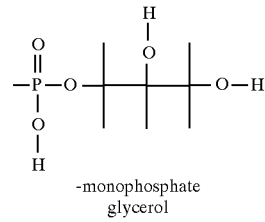
-monophosphate glycerol

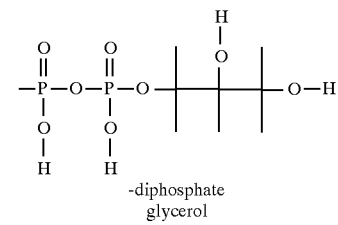
-diphosphate glycerol

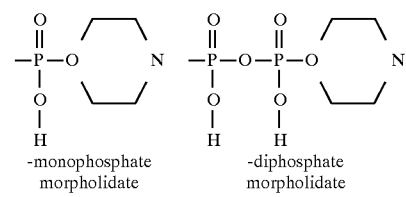
-monophosphate morpholidate     -diphosphate morpholidate

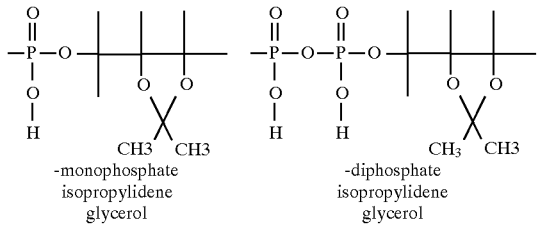
-monophosphate isopropylidene glycerol     -diphosphate isopropylidene glycerol Corresponding triphosphate derivatives have corresponding structures.

According to the invention, acyclovir monophosphate (ACV-MP), acyclovir diphosphate (ACV-DP), acyclovir triphosphate (ACV-TP), acyclovir monophosphate glycerol (ACV-MP-G), acyclovir diphosphate glycerol (ACV-DP-G), acyclovir monophosphate morpholidate (ACV-MP-morpholine), acyclovir diphosphate morpholidate (ACV-DP-morpholine), acyclovir diphosphate morpholidate (ACV-DP-morpholine), acyclovir phosphomethylene-diphosphonate (ACV-PMDP), acyclovir monophosphate isopropylidene glycerol (ACV-MP-isoP-G), acyclovir diphosphate isopropylidene glycerol (ACV-DP-isoP-G), either alone or combined, are prepared in a suitable topical pharmaceutical formulation and applied to the cutaneous lesions of an HSV-infected individual. The compounds ACV-MP, ACV-DP, ACV-TP, ACV-DP-G, ACV-PMDP, the morpholine derivative of acyclovir, and the acyclovir isopropylidene glycerol derivatives described, are non-lipid, water soluble phosphate esters, and are therefore preferably provided in an aqueous base topical formulation.

Surprisingly, we have discovered that the monophosphates of acyclovir, and we expect that monophosphate and polyphosphate derivatives of other nucleosides will, exhibit enhanced topical anti-HSV activity. We have also demonstrated that salts of monophosphate, diphosphate and triphosphate and phosphomethylenediphosphonate derivatives of nucleoside analogues can be easily prepared, and that such salts exhibit enhanced solubility in aqueous media, i.e., cream, gels, or other aqueous dispersions. Moreover, such salts are soluble in polyethylene glycol media which provides a unique mucosal or cutaneous dispersion.

Other polyphosphate esters of nucleotide analogues that are useful in the methods of the invention include mehtylene and this-linked polyphosphate nucleoside analogues s as well as mono- and polyphosphoamidate and mono- and polyphosphothiorate nucleoside analogues.

Similarly, monophosphates, diphosphates, and other phosphate esters of other antiherpes simplex nucleosides will exhibit enhanced topical activity as those above noted. The following herpes antiviral nucleosides exhibit enhanced activity as phosphate esters:

1-beta-D-arabinofuranosyl-E-5-(2-bromovinyl)uracil [broavir; BV-araU];

2'-fluorocarbocyclic-2'-deoxyguanosine;

6'-fluorocarbocyclic-2'-deoxyguanosine;

1-(beta-D-arabinofuranosyl)-5(E)-(2-iodovinyl)uracil;

(1r-1α, 2β, 3α)-2-amino-9-(2,3-bis(hydroxymethyl) cyclobutyl)-6H-purin-6-one (SQ 34,514) 9H-purin-2-amine, 9-((2-(1-methylethoxy)-1-((1-methylethoxy) methyl)ethoxy)methyl)-(9CI) (HOE 602)

triflurothymidine;

9-[(1,3-dihydroxy-2-propoxy)methyl]guanine;

5-ethyl-2'-deoxyuridine;

E-5-(2-bromovinyl)-2'-deoxyuridine;

5-(2-chloroethyl)-2'-deoxyuridine;

1-(2-deoxy-2-fluoro-beta-D-arabinofuranosyl)-5-iodocytosine (FIAC);

1-(2-deoxy-2-fluoro-beta-D-arabinofuranosyl)-5-iodouridine (FIAU);

buciclovir;

6-deoxyacyclovir;

9-(4-hydroxy-3-hydroxymethylbut-1-yl)guanine;

E-5-(2-iodovinyl)-2'-deoxyuridine;

5-vinyl-1-beta-D-arabinofuranosyluracil (V-araU);

1-beta-D-arabinofuranosulthymine (Ara-T);

2'-nor-2'deoxyguanosine (2'NDG);

9-(4-hydroxy-3-hydroxymethylbut-1-yl)guanine (penciclovir, BRL 3912)

1-beta-D-arabinofuranosyladenine (Ara-A; vidarabine)

The monophosphate, diphosphate and triphosphate esters have the general formula

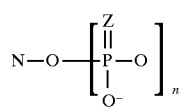

wherein N is an anti-herpes simplex virus nucleoside analog; Z is O, S, or NH; and n is 1 or 2; or alternatively have the following formula

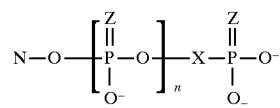

wherein N is an anti-herpes simplex virus nucleoside analog;
Z is O, S or NH;
X is O, C or S; and
and n is 1 or 2.

Accordingly, the phosphoesters can be phosphate, phosphothiorate, or phosphoramidate, and the diesters and triesters may have bridging atoms other than oxygen, for example, 2,3-μ-thiotriphosphate esters, or 2,3μ-methylenediphosphonate.

Contrary to expectation, these nucleoside analog phosphates can surprisingly pass through the cell membrane of HSV-infected skin cells and reduce the rate of viral replication by inhibiting the HSV DNA polymerase. The mono- and di-phosphate nucleosides of the invention are converted to their triphosphates by cellular anabolic phosphorylation (s) but the triphosphate analogs inhibit the HSV DNA polymerase directly without the need to inhibit cellular DNA polymerase. The invention also provides for pharmaceutical formulations of the nucleoside analog mono-, di- and triphosphates in concentrations that can be applied topically to effectively reduce the proliferation of HSV in infected skin cells. DNA chain-terminating dideoxynucleoside phosphates, when applied to the skin in a suitable topical formulation, will similarly reduce HSV replication. These include acyclovir, ganciclovir, penciclovir, BVaraU dideoxycytidine, dideoxythymidine, dideoxyguanosine, dideoxyadenosine, dideoxyinosine, 3'-azidodideoxythymidine, dideoxyhydrodideoxythymidine (d4T) and other dideoxynucleoside analogs such as those described in copending U.S. patent application Ser. No. 07/373,088 which is hereby incorporated by reference.

Salts of these compounds can be easily prepared and such salts should exhibit enhanced solubility in aqueous media, i.e., cream, gels, or other aqueous dispersions. Typically, useful salts of these compounds include sodium, potassium, lithium, ammonium, or hydrogen salts. Any physiologicallly acceptable cation known to those skilled in the art may also be used. Moreover, such salts are usable and effective in polyethylene glycol creams and lotions which provide a favorable mucosal or cutaneous dispersion.

The various phosphate esters of these compounds may be prepared essentially as described below for acyclovir.

Synthesis of Acyclovir Phosphate Esters

The present invention provides methods for the synthesis of acyclovir mono- and diphosphates, acyclovir monophosphate morpholidates, acyclovir mono- and diphosphate glycerols, and acyclovir mono- and diphosphate 1,2-isopropylidene glycerol.

Acyclovir monophosphate can be prepared from acyclovir according to the method of Yoshikawa, M., et al., *Bull. Chem. Soc. Japan* 42:3505–3508 (1969) as modified by the method of Toorchen, D. and Topal, M., *Carcinogenesis* 4:1591–1597 (1983), and exemplified in Example 1. Acyclovir diphosphate can be prepared, in the manner of other nucleoside analogues, by the method of Ott, D. G., et al., *Anal. Biochem.* 21:469–472 (1967), using either tributylammonium phosphate or tributylammonium pyrophosphate as the phosphate donor.

Methods for the preparation of acyclovir diphosphate glycerol are presented in Examples 2 through 4. In general, the nucleoside phosphate glycerols are prepared in a manner similar to that for the preparation of phosphatidyl nucleosides. In the approach described in Example 3, acyclovir phosphate is activated by the addition of a leaving group, for example, morpholine, according to Example 2, and condensed with glycerol-3-phosphate dicyclohexylammonium salt in the presence of N,N'-dicyclohexylcarbodiimide (DCC). Alternatively, as described in Example 4, glycerol phosphate, having the reactive hydroxyl groups protected by an isopropylidene moiety, is activated by addition of morpholidate, and then condensed with acyclovir monophosphate under the conditions described for Example 2.

A number of acyclovir-diphosphate-diglycerides (ACV-DP-DG) containing various acyl chains have been prepared in the past by the condensation of the appropriate diacylphosphatidic acid morpholidate (PA-Morpholidate) and acyclovir monophosphate (ACV-MP.) A method by which the procedure can be carried out is described by Agranoff, B. and Suomi, W., *Biochem. Prep.* 10:47–51 (1963). Alternatively, the morpholidate of the nucleoside monophosphate is prepared and condensed with a phosphatidic acid as described in U.S. patent application Ser. No. 07/706, 873 entitled "Liponucleotide Synthesis," and by Hong, et al., British Patent Application No. 2,168,350.

The chemical methods above are generally disclosed in terms of their general application to the preparation of compounds of the invention. Occasionally, the reaction may not be applicable as described to each compound included within the disclosed scope. The compounds for which this occurs will be readily recognized by those skilled in the art. In all such cases, either the reactions can be successfully performed by conventional modifications known to those skilled in the art, e.g. by appropriate protection of interfering groups, by changing to alternative conventional reagents, or by routine modification of reaction conditions. Alternatively, other reactions disclosed herein or otherwise conventional will be applicable to the preparation of the corresponding compounds of the invention. In all preparative methods, all starting materials are known or readily preparable from known starting materials. Unless otherwise indicated, all parts and percentages are by weight.

Synthesis of Nucleoside Monophosphates, Diphosphates and Triphosphates and Nucleoside Phosphate Analogues: The methods for synthesizing nucleoside monophosphates by reacting the nucleoside with phosphorus oxychloride are described in copending U.S. patent applications Ser. No. 07/373,088 and Ser. No. 08/060,258 and as previously described (Yoshikawa et al., *Bull. Chem. Soc. Japan* 42:3505–3508, 1969; Toorchen, D. and Topal, M., *Carcinogenesis* 4:1591–1597, 1983). Nucleoside diphosphates are prepared by the method of Ott, D. G. et al. (*Anal. Biochem.* 21:469–472, 1967).

Nucleoside triphosphates are prepared by the method of Seela and Röling (*Nuc. Acids Res.* 20:55–61, 1992), or from the nucleoside monophosphates by the method of Moffat and Khorana (*J. Am. Chem. Soc.* 83:663, 1991), or by the method of Hoard and Ott (*J. Am. Chem. Soc.* 87:1785–1788, 1963). The examples below present the details of some syntheses useful for preparing phosphate esters of nucleosides and nucleoside analogs.

Other nucleoside phosphate analogues including nucleoside phosphorothioates, nucleoside phosphoramidates, nucleoside phosphonates and nucleoside phosphorofluoridates can be synthesized using methods well known to those skilled in the art and summarized, for example, by D. W. Hutchinson (*The synthesis, reactions and properties of nucleoside mono-, d-, tri-, and tetraphosphates and nucleotides with changes in the phosphoryl residue.* In *Chemistry of Nucleotides and Nucleosides,* L. Townsend, ed., 1991 at pp 81–146 and references therein). The common syntheses are summarized as follows.

(1) Nucleoside Phosphorothioates are analogues of nucleotides in which one or more of the phosphoryl oxygen atoms have been replaced by sulfur. Early methods of synthesis reacted a protected nucleoside and tris(1-imidazolyl) phosphane sulfur whereas more recent syntheses replace the latter reagent with thiophosphoryl-chloride ($PSCl_3$). A nucleoside phosphoranilidate can be converted into a phosphorothioate by treatment with sodium hydroxide and carbon disulfide. Nucleoside 5'-phosphorothioates can result from direct sulfurization of nucleoside 5'-phosphites. Purine nucleoside 2'(3') -phosphorothioates can be synthesized by reacting their 2',3'-O-di-n-butylstannylene derivatives with thiophosphoryl chloride followed by alkaline hydrolysis.

(2) Nucleoside Phosphoramidates are analogues in which one or more phosphoryl oxygen atoms have been replace by nitrogen creating a P-N bond which is considerably more labile than the P-S bond of nucleoside phosphorothioates even under mildly acidic conditions. Syntheses of these compounds include the phosphorylation of aminonucleosides and the treatment of nucleoside azides with triesters of phosphorous acid. Lipophilic nucleoside phosphoramidates may be particularly useful anti-HSV compounds because of their ability to be more readily taken up by cells where they are hydrolyzed into biologically active compounds.

(3) Nucleoside Phosphonates are compounds in which a phosphoryl oxygen is replaced by carbon creating a stable P-C bond and having decreased acidity of the P-OH groups when the phosphorus atom is substituted with an electron-donating alkyl group in place of the oxygen. Nucleoside phosphonates are easily prepared from nucleoside halides by those skilled in the art using either the Arbusov or the Michaelis-Becker reactions. Nucleoside 5'-phosphonates can be synthesized from 2',3'-protected 5'iodo-5'-deoxynucleosides using methods well known to those skilled in the art. Isosteric nucleoside 5'-phosphonates, in which the 5'-oxygen is replaced with a methylene group, are synthesized by coupling a suitably-protected nucleoside 5'-aldehyde with diphenyl triphenylphosphoranylidenemethylphosphonate to give a α,β-unsaturated phosphonate diester that is then reduced and deprotected at the phosphoryl residue to give the phosphonate. Isosteric nucleoside 3'-phosphonates are synthesized starting from the phosphonylated ribose-1 chloride which is coupled with the heavy metal salt of a purine or pyrimidine. Phosphonates are generally less polar than their phosphate counterparts and therefore are useful as anti-HSV agents because they are more readily taken up by cells when applied topically.

(4) Nucleoside Phosphorofluoridates are analogues of mononucleotides. Treatment of nucleoside 5'-phosphates with 2,4-dinitrofluorobenzene produces the nucleoside 5'phosphorofluoridates via the 2,4-dinitrophenylester of the nucleotide.

(5) Other Nucleoside Polyphosphate Analogues include those in which atoms other than oxygen have been substituted between the α,β-phosphorus atoms in di- and triphosphates of nucleosides or between the β,γ-phosphorus atoms in nucleoside triphosphates (including those listed in Table III at page 119 of D. W. Hutchinson, In *Chemistry of Nucleotides and Nucleosides*, L. Townsend, ed., 1991). Usually, the α,β-analogues are prepared by condensing a 2',3'-O-protected nucleoside with the pyrophosphate analogue with the aid of DCC or by nucleophilic displacement reactions involving the displacement of a toluene-sulfonyl (tosyl) residue from the 5'-position of the sugar residue of the tosyl nucleoside by methylene bisphosphonate ion.

Figure 2:
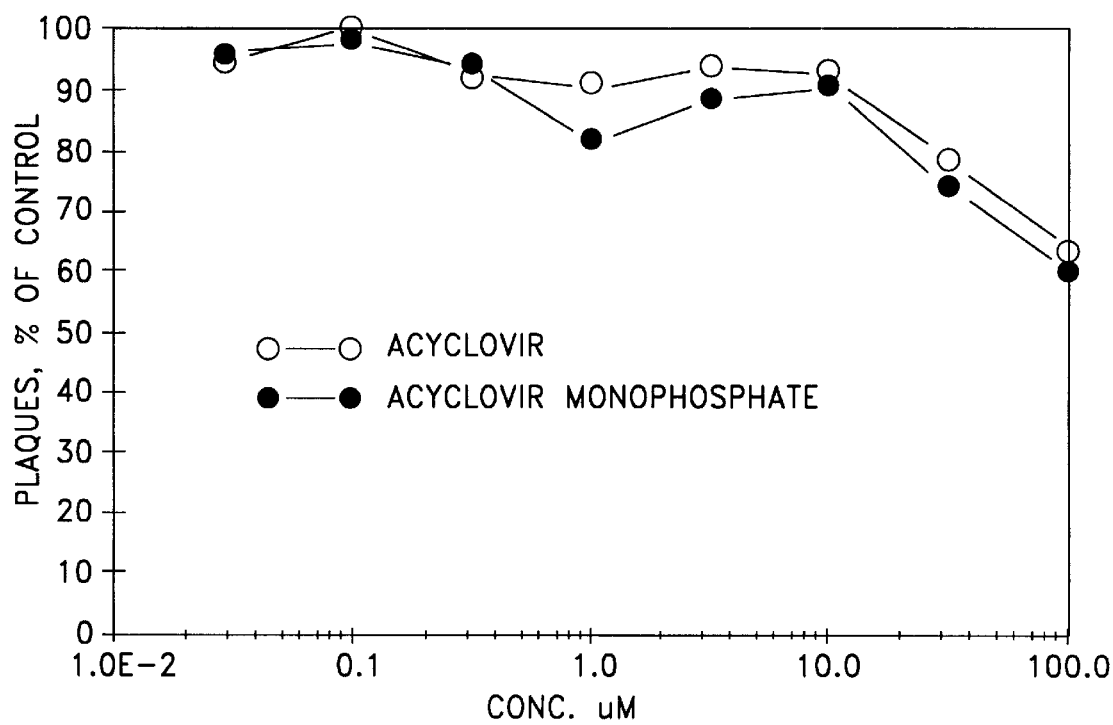
FIG. 2 illustrates the comparative effect of acyclovir and acyclovir monophosphate on the replication of HSV-DM.21 TK mutant in vitro.

The acyclovir derivatives of the invention, comprising ACV-MP, ACV-DP, ACV-TP, ACV-MP-glycerol, ACV-DP-glycerol, ACV-MP-isopropylidene glycerol, ACV-DP isopropylidene glycerol and ACV-P-methylenediphosphonate were found to have particular efficacy in topically treating the herpetic lesions of acyclovir-resistant HSV-1 infections. Example 7 demonstrates that infection of cultured cells with wild type isolates and laboratory strains of HSV can be treated with equal success using acyclovir, acyclovir monophosphate (Example 7; FIG. 1). For these viral infections in Wi38 fibroblasts, both acyclovir and acyclovir monophosphate have the same $IC_{50}$ of about 1 or 2 $\mu$M concentration. However, when the same cultured cell system is infected with an acyclovir-resistant strain of virus, HSV-DM.21, lacking the thymidine kinase necessary to convert acyclovir to acyclovir monophosphate, acyclovir and acyclovir monophosphate are ineffective in reducing the number of viral plaques (Example 7; FIG. 2).

Figure 3:
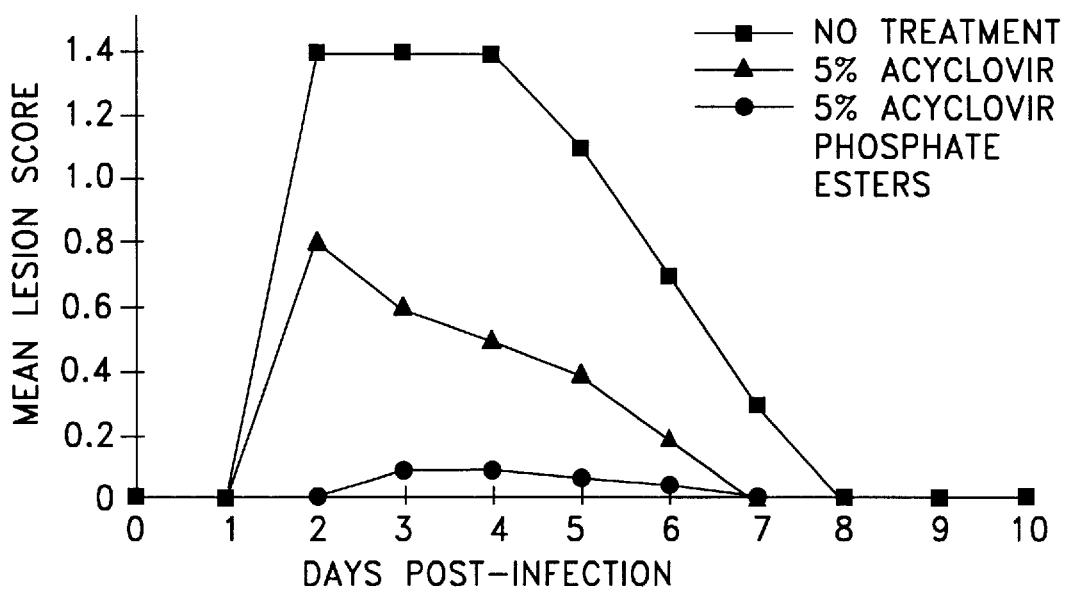
FIG. 3 illustrates the comparative effect of topical acyclovir and acyclovir phosphate esters on acyclovir-resistant HSV-1 infections of the TK-deficient type in HRS/J mice.
Figure 4:
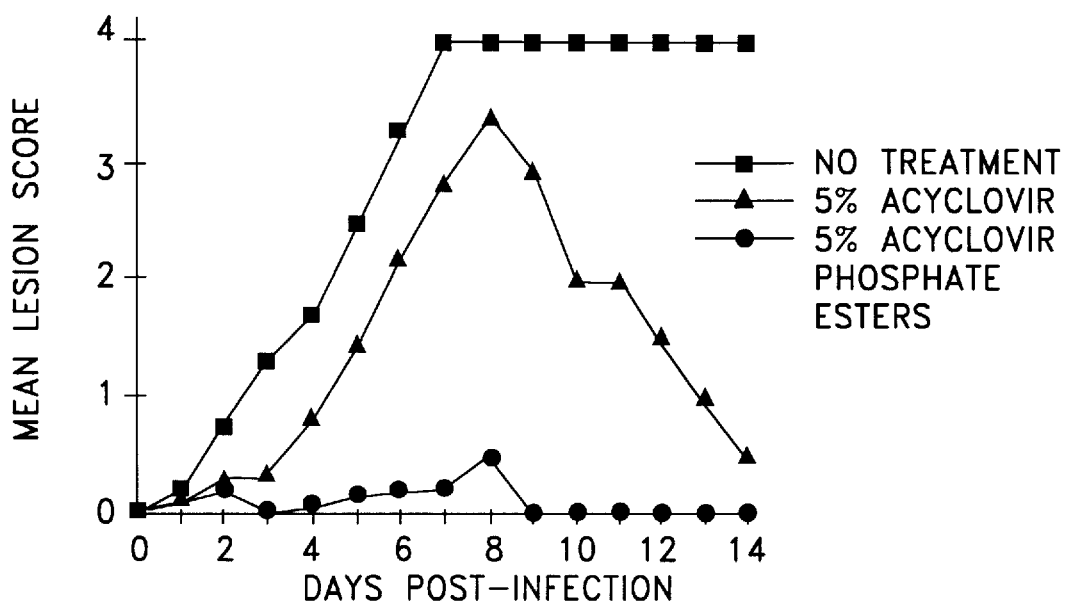
FIG. 4 illustrates the comparative effect of topical acyclovir and acyclovir phosphate esters on acyclovir-resistant HSV-1 infections of the TK-altered type in HRS/J mice.

The efficacy of acyclovir phosphate esters with respect to acyclovir-resistant cutaneous HSV-1 infections is surprising in view of the cultured cell in vitro data above. Acyclovir phosphate esters applied in an aqueous cream to the herpetic lesions of mice infected with acyclovir-resistant HSV-1 were substantially more effective than native acyclovir in reducing the number of such lesions (Example 9; FIGS. 3 and 4).

Accordingly, in view of these results, it is believed that in vitro incorporation of acyclovir, and acyclovir phosphates, proceed through a different mode of operation than in vivo as a topically applied lotion.

Topical Formulations of Nucleoside Analogue Phosphates

The nucleoside analogue derivatives of the invention as previously described can be prepared for topical use by incorporation into a variety of formulations known to those in the art as useful and convenient for dermatological use. The nucleoside analogue derivatives are water soluble, and accordingly an aqueous solution, water-in-oil emulsion, or an aqueous cream are highly preferred formulations. Water solubility of the acyclovir and other nucleoside monophosphates can be enhanced through the preparation of salts, such as sodium, potassium, ammonium, or hydrogen. In a particularly preferred formulation, the active ingredient is prepared in a polyethylene glycol (PEG) vehicle. Alternatively, the active ingredients can be topically applied in a dry powder formulation, using an insoluble powder, such as starch or talc as a diluent or carrier.

The vehicle is an important component of some topical formulations, because it can be selected to enhance penetration, to prolong the duration of activity, or to meet requirement of the site of application. For example, a formulation for application to the callous parts of the body, such as the palms of the hand or bottoms of the feet, can include a penetration enhancing agent such as dimethylsulfoxide propylene glycol or azone™; a powdery formulation can be selected for application to the intertriginous zones such as the crotch, inner elbow or between the fingers or toes. The formulation can also be made up to contain various organic polymers or other compositions known to those of skill in the art to give sustained release of the active antiviral acyclovir derivatives.

A multitude of appropriate topical formulations can be found in the formulary known to all pharmaceutical chemists: Remington's Pharmaceutical Sciences, 15th Edition, 1975. Mack Publishing Company, Easton, Pa. 18042. (Chapter 87: Blaug, Seymour). These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

The concentration of active ingredient in the topical formulations of the invention can be from about 0.01 gm % to 100 gm %; preferably from about 0.1 gm % to 50 gm %; most preferably from about 1 gm % to about 15 gm %. The formulations can further comprise effective concentrations of other agents which help to promote penetration of the skin and healing, as described in the above-referenced formulary and are well known to those of ordinary skill in the art.

Efficacy of topical formulations containing the active phosphate esters of the invention can be evaluated using conventional testing procedures, known to those of skill in the art. For example, a particularly expeditious procedure is the murine "orofacial model," as described by Ellis, M., et al., *Antimicrobial Agents and Chemotherapy* 33:304–310 (1989). In this test system, the pathogenesis of HSV in mice scarified and inoculated on the snout has been shown to be a reasonable model of the disease cycle of cutaneous HSV infection in the immunocompromised host.

The formulations can be applied to the herpetic lesions of the affected skin repeatedly; for example once, twice, or several times a day, and the treatment can be extended for several days until healing is achieved. The risk of incidence of toxicity and irritation is minimal.

Without further elaboration, it is believed that one skilled in the art can, using the preceding description, utilize the invention to its fullest extent.

The present invention is described below in additional detail using the following examples, but the methods described below are applicable to all methods within the scope of the invention and the invention is not limited to the examples given. The following preferred embodiments are, therefore, to be construed as merely illustrative and not limitative of the remainder of the disclosure in any way whatsoever.

EXAMPLE 1

Phosphorylation of Acyclovir Nucleoside Derivatives

We prepared acyclovir nucleoside derivatives through the following methods. Unprotected acyclovir was reacted with $POCl_3$ in trimethyl phosphate ($(CH_3O)_3PO$) was performed essentially as described by Yoshikawa et al. *Tetrahedron Letters* 50:5065–5068 (1967); and Yoshikawa, M., Kato et al. *Bull Chem. Soc. Japan* 42:3205–3208 (1967). To a cooled solution (0° C.) of 2 M POCl$_3$ in 300–400 ml trimethyl phosphate, acyclovir (1 M) was added dropwise with stirring, the reaction temperature being held constant between 0° and 5° C. The progress of the reaction was monitored by means of HPLC using a Mono Q HR 5/5 anion exchange column (Pharmacia, Uppsala, Sweden). Typically, 5 μl of the reaction mixture was neutralized with aqueous sodium hydroxide (final pH 7) and injected on the column.

Elution was performed as follows: washing with water, elution with 0.1 M ammonium carbonate, NH$_4$HCO$_3$, which elutes the acyclovir monophosphate, followed by a linear gradient of 0.1–0.6 M NH$_4$HCO$_3$ which elutes some higher phosphorylated products. The reaction was mostly completed within 45 to 75 minutes as determined by this method, and the reaction product was hydrolyzed and neutralized with 2 volumes of aqueous sodium hydroxide to final pH of 7.

Purification of the product compound was conducted as described above for the analysis of the reaction mixture. By this method, 0.8 moles of acyclovir monophosphate were prepared and purified with a Q Sepharose fast flow column using the same elution conditions.

Yields varied between 80% and 96% after repeated lyophilization from water.

TLC analysis (Silica 60/F254 Plates, Merck) showed a single U.V. and Pi positive spot, using the developing system 1-propanol/25% NH$_3$/H$^2$O (20:20:3 by volume).

EXAMPLE 2

Preparation of Acyclovir-monophosphomorpholidate

Acyclovir-monophosphate (5 mmol) and morpholine (20 mmol) were suspended in t-butanol (50 ml) and heated under gentle reflux while N,N'-dicyclohexylcarbodiimide (DCC, 20 mmol) dissolved in t-butanol (50 mmol) was added dropwise over a period of 1 hour. The mixture was stirred under reflux for 12 to 36 hours and evaporated to dryness. The residue was triturated with ether and washed by decantation with the same solvent. The product was purified by recrystallization from methanol-ether mixtures.

EXAMPLE 3

Preparation of sn-Glycero-3-diphospho-acyclovir from Acyclovir-monophosphomorpholidate Acyclovir monophosphomorpholidate (2 mmol), prepared as described in Example 2, was dissolved in dry pyridine (20 ml) and evaporated to dryness under vacuum. The process of dissolving the residue in pyridine and evaporation was repeated three additional times to remove traces of water from the compound. Glycerol-3-phosphate di-monocyclohexylammmonium salt (3 mmol) was added to the dried residue and the mixture was dissolved in 20 ml of pyridine and stirred under inert atmosphere at 60° C. for 12–36 hours. The solvent was evaporated under vacuum and the residue was titrated with ether and the resulting solid was purified by ion exchange chromatography over DEAE sephadex column (2.5 cm×30 cm) using a linear gradient of ammonium bicarbonate (10 mmol to 300 mmol, 500 ml each). Fractions containing pure product (identified by using TLC and analytical HPLC) were pooled and lyophilized to furnish the title compound.

EXAMPLE 4

Preparation of sn-Glycero-3-diphospho-acyclovir from 1,2-isopropylidene-sn-glycero-3-monophosphomorpholidate A. Preparation of 1,2-Isopropylidene-sn-glycero-3-phosphate Phosphorous oxychloride (25 mmol) was added dropwise over a period of 30 minutes to a mixture of 1,2-Isopropylidene-glycerol (20 mmol) (Sigma, St. Louis, Mo.) and triethylamine (100 mmol) that was cooled to 0° C. After stirring the mixture at 0° C. for 10 to 90 minutes. Water (1 ml) was added to stop the reaction. The mixture was then dissolved chloroform (500 ml) and washed with water (3×100 ml). The water wash solutions were combined and back extracted with chloroform (50 ml) and lyophilized. The product was used immediately for subsequent reactions without any additional purification.

B. Preparation of 1,2-isopropylidene-sn-glycero-3-monophosphomorpholidate 1,2-isopropylidene-sn-glycero-3-phosphate, prepared as described in (A), was condensed with morpholine to prepare 1,2-isopropylidene-sn-glycero-3-monophosphomorpholidate, according to the procedure described for the preparation of acyclovir phosphomorpholidate in Example 2.

Reaction of the intermediate compound, 1,2-isopropylidene-sn-glycero-3-monophosphomorpholidate, with acyclovir monophosphate under the conditions described in Example 2, yielded 1,2-isopropylidene-sn-glycero-3-monophosphomorpholidate.

1,2-isopropylidene-sn-glycero-3-diphospho-acyclovir (1 mmol) was dissolved in 50 to 90% aqueous acetic acid and stirred at room temperature for a period of 4 to 12 hours and the crude glycero-3-diphospho-acyclovir product was purified as described above.

EXAMPLE 5

Preparation of sn-glycero-3-phospho-acyclovir 1,2-Isopropylidene-sn-glycero-3-phosphate, 1 mM (prepared as in Example 4B), and acyclovir (1 mM), were suspended in dry pyridine (10 ml) and DCC (4 mmol). Dissolved pyridine (4 ml) was added and the mixture stirred at 25° C. to 60° C. for 12 to 72 hours. The solvent was evaporated and the residue was titrated with ether. The crude product was purified by ion exchange chromatography as described in Example 3. The isopropylidene-protecting group was then removed from the product by treating with aqueous acetic acid to furnish the title compound.

Alternatively, the title compound was also prepared by using 2,4,6-triisopropylbenzenesulfonyl chloride (TPS-Cl) as the condensing agent.

EXAMPLE 6

Preparation of Acyclovir Phosphate Ester Mixture by the Alkaline Hydrolysis of Acyclovir Diphosphate Dipalmitoylglycerol Acyclovir-diphosphate-dipalmitoylglycerol (1 mmol) was dissolved in chloroform, to which methanolic sodium hydroxide (2.1 mmol) was added. The reaction was carried for 20 to 90 minutes and the progress was monitored by TLC. Upon completion of the reaction, Dowex-50 X-2 (H+) was added to the reaction mixture to adjust the pH to 7. The resin was separated by filtration and the filtrate was lyophilized and the crude product was purified as described in Example 1.

EXAMPLE 7

Preparation of Nucleoside Triphosphates from Mononucleosides

Preparations of 5' triphosphates of deoxyribonucleotides, dideoxyribonucleotides and analogs involves a series of reactions as outlined immediately below.

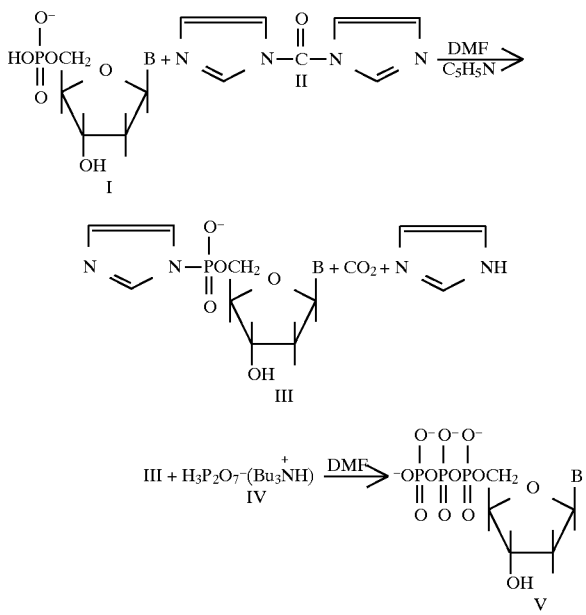

Nucleotide analogue monophosphate synthesis is described in the co-pending U.S. patent application Ser. No. 08/060,258, filed May 12, 1993, and in Example I. Further methods are as follows:

A nucleotide (I) and excess 1,1'-carbonyldiimidazole (II) are reacted for about 1 hour at room temperature to form an imidazolidate (III). Unreacted 1,1'-carbonyldiimidazole is decomposed with methanol before an excess of inorganic pyrophosphate (IV) is added. This eliminates the formation of inorganic polyphosphates which would have to be subsequently removed from the reaction materials. Phosphorylation is allowed to proceed to completion at about 24 hours after addition of the inorganic pyrophosphate (IV) and then the nucleoside triphosphate product (V) is purified by anion-exchange chromatography on DEAE-cellulose followed by conversion of the product to a salt such as a sodium salt. Because the nucleotide (I) and the imidazolidate (III) can react together to form a symmetrical pyrophosphate by-product, the anion-exchange chromatography on DEAE-cellulose is carried out at a lower pH where the desired product (V) has less charge than the undesirable by-product, thus allowing separation of the two compounds.

One reagent used in the synthesis is tributylammonium pyrophosphate which is made by the following procedure. To an aqueous solution of pyridinium pyrophosphate, obtained by passing a solution of tetrasodium pyrophosphate decahydrate (446 mg, 1 mmole) through a column of Dowex 50W-X4™ (pyridinium) resin (17 ml) is added tributylamine (0.24 ml, 1 mmole). The solution is concentrated under vacuum and the residue is then dried by consecutive addition and evaporation of anhydrous pyridine followed by addition and evaporation of two 10-ml portions of N,N-dimethylformamide (DMF).

The synthesis of nucleoside triphosphates is accomplished by the following method. To a solution or suspension of the mono-nucleotide (0.1 mmole) as the anhydrous tributylammonium salt, in 1 ml of DMF, is added 1,1'-carbonyldiimidazole (80 mg, 0.5 mmole) in 1 ml DMF. The combination is mixed for 30 minutes and then held in a desiccator at room temperature for 4–12 hr before it is treated with 33 µl (0.8 mmole) of methanol and allowed to react for 30 min at RT. Tributylammonium pyrophosphate (0.5 mmole) in 5 ml DMF is added and vigorously mixed and then the mixture is held in a desiccator at RT for about 24 hr to allow imidazolium pyrophosphate to precipitate. The precipitate is removed and washed with four 1 ml portions of DMF by centrifugation and resuspension in the DMF resulting in about 80–100% purity. The supernatant is treated with an equal volume of methanol and evaporated to dryness under vacuum. The residue is chromatographed on a 2×20 cm column of DEAE-cellulose with a linear gradient of triethylammonium bicarbonate (a 3 l gradient of about 0 to 0.4 M at pH 5–7.5 and fractions are collected and assayed spectrophotometrically to identify fractions containing nucleoside triphosphates. The appropriate fractions are evaporated under vacuum and the triethylammonium nucleoside triphosphate is dissolved in methanol to a concentration of about 0.05 M and five volumes of an acetone solution of sodium perchlorate (15 equiv) is added to form a precipitate of the sodium salt of the nucleoside triphosphate. It will be understood by those skilled in the art that other salts of the nucleoside triphosphate could be made by the appropriate precipitation reactions. The precipitated salt is collected by centrifugation, washed with four 1-ml portion of acetone and dried under vacuum over phosphorus pentoxide.

Additional procedures are available for synthesis of nucleoside triphosphates including the one presented in the next example.

EXAMPLE 8

Synthesis of Nucleoside Mono-, Di- and Tri-phosphates Using 2,2,2-Tribromoethyl Phosphoromorpholinochloridate Using the method essentially of van Boom, et al. (*Tetrahedron Lett.* 32:2779–2782, 1975), mono-, di- and tri-phosphates of ribonucleosides and their derivatives are prepared from a single intermediate. In general, the reactions include reacting a monofunctional reagent (2,2,2-tribromoethyl phosphoromorpholinochloridate) with a ribonucleoside (or its derivative) to make phosphotriester derivatives with a 2,2,2-tribromoethyl protecting group attached to the ribonucleoside (i.e., to produce a ribonucleoside 5'-phosphomorpholidates or ribonucleoside 5'-phosphomorpholidate derivatives). The protecting group is removed by a Cu/Zn coupling reaction with acidic deblocking and neutralization to produce the mono-, di-, and tri-phosphates depending on the acid used in the deblocking step and the ammonium salt used in the neutralizing step. That is, to obtain the monophosphate ribonucleoside, HCl and ammonia are used; to obtain the diphosphate ribonucleoside, the mono(tri-n-butylammonium) salt of phosphoric acid is used; to obtain the triphosphate ribonucleoside, bis(tri-n-butylammonium) pyrophosphate is used.

The general reactions are diagrammed as follows:

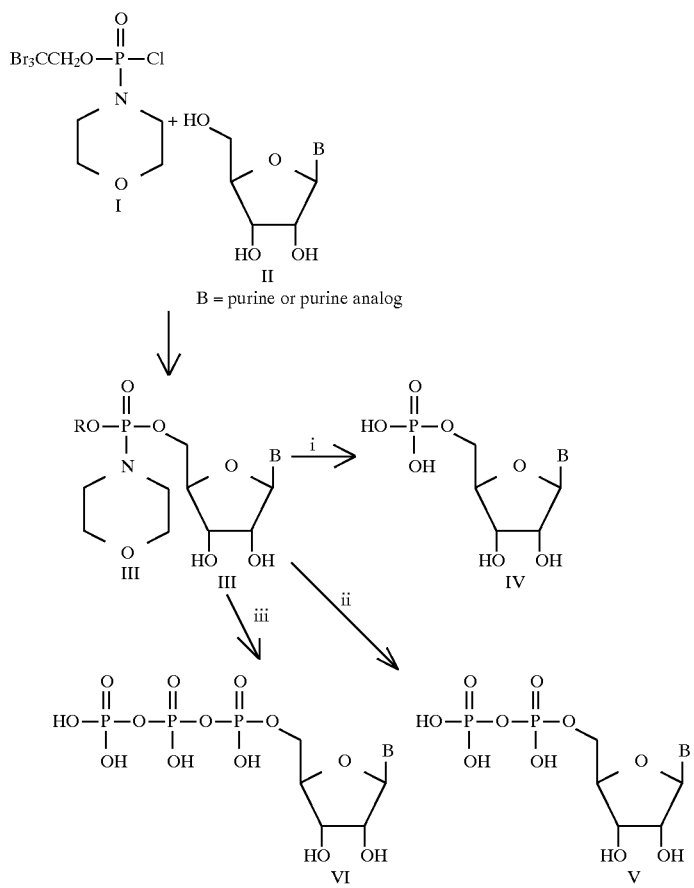

B = purine or purine analog

The monofunctional reagent (I) 2,2,2-tribromoethyl phosphoromorpholinochloridate is prepared by reacting 2,2,2-tribromoethyl phosphorodichloridate and morpholine in anhydrous ether, from which the reaction product is removed and recrystallized using cyclohexane/n-pentane using methods well known in the art. The crystalline 2,2,2-tribromoethyl phosphoromorpholinochloridate has a m.p. of 79° C.

The monofunctional reagent (2 mmole) is mixed with 1 mmole of the nucleoside or its derivatives in anhydrous pyridine at 20° C. for 48 hr; then the reaction mixture is fractionated chromatographically (B. J. Hunt & W. Rigby, Chem. & Ind. 1868, 1967) to yield colorless solids of nucleotides (III). Treatment of the nucleotides with Cu/Zn couple in anhydrous DMF for 10 min at 20° C. followed by filtration to remove excess Cu/Zn gives the nucleoside phosphoromorpholidates.

The nucleoside phosphoromorpholidates are then treated with different acids and ammonia sources to yield either mono-, di-, or tri-phosphates. For monophosphate, the phosphoromorpholidate is treated with 0.01 N HCl, pH 2 for 2 hr at 20° C. and then neutralized with aqueous ammonia (pH 9) and purified over a column of Sephadex G-25™.

Similarly the nucleoside 5'-triphosphate is obtained by reacting the phosphoromorpholidate (0.1 mmole) in 2 ml of anhydrous DMF with 0.5 mmole of bis(tri-n-butylammonium) pyrophosphate in 2 ml of anhydrous DMF at 20° C. for 3 hr under conditions that exclude moisture. The reaction product is concentrated under vacuum, treated with Dowex 50™ (ammonium form), and purified on a 2×25 cm column of DEAE cellulose using a 3 l linear gradient of 0.0 to 0.3 M $Et_3NH_2CO_3$ solution.

The nucleoside 5'-diphosphate is obtained by reacting the phosphoromorpholidate (0.1 mmole) with 0.6 mmole of mono(tri-n-butylammonium)phosphate in 4 ml of anhydrous pyridine at 20° C. for 3 hr under conditions that exclude moisture and the reaction product is similarly concentrated and purified. Alternatively, the phosphotriester derivatives (III) can be converted directly into the corresponding nucleoside diphosphates by treatment with Zn-dust in pyridine solution containing mono(tri-n-butylammonium) phosphate. That is 1 mmole of reagent III is added to a stirred solution of 15 ml anhydrous pyridine containing 0.1 g of finely divided Zn and 12 mmole mono(tri-n-butylammonium)phosphate under conditions that exclude moisture for about 48 hr at 20° C. Then the reaction mixture is centrifuged to pellet the Zn and the supernatant is co-evaporated three times with 15 ml of water at each step before purification on DEAE cellulose.

EXAMPLE 9

Synthesis of Acyclovir Triphosphates (1) Acyclovir-5'-triphosphate, triethylammonium salt, synthesis. Acyclovir (25 mg, 0.1 mmol) is dissolved in trimethyl phosphate (250 μl, 1.07 mmol) and $POCl_3$ (18.5 μl, 0.2 mmol) are added. The mixture is stirred for 1.5 h at 0° C. and then a mixture of 0.5 M bis(tri-n-butylammonium) pyrophosphate in 1 ml of anhydrous DMF and 1 ml of tri-n-butylamine are added with vigorous stirring for 1 min.; the solution is neutralized with 1 M aqueous $Et_3NH_2CO_3$ solution, pH 7, and evaporated to dryness under vacuum. The residue is purified on a 2.6×30 cm column of DEAE-sephadex using a linear gradient of $Et_3NH_2CO_3$, pH 7 (1 l $H_2O$/1 l 0.7 M TBK) solution to yield a colorless solid with a UV ($H_2O$) $\lambda_{max}$ of 258 nm.

EXAMPLE 10

Synthesis of Acyclovir-phosphomethylenediphosphonate

The synthesis is essentially as described in Method 1 of Myers et al. (J. Am. Chem Soc. 85: 3292–3295, 1963). A nucleoside 5'-phosphoramidate is reacted with methylenediphosphonic acid to produce the phosphonic acid analogs of the nucleoside polyphosphate. Alternatively, using Method 2 of Myers et al. (id.), a nucleoside monophosphate is reacted with methylenediphosphonic acid using dicyclohexylcarbodiimide (DCC) as the condensing agent.

According to Method 1, methylenediphosphonic acid is obtained by hydrolysis in concentrated HCl of its tetraethyl ester which is prepared by the reaction of methylene iodide with excess triethyl phosphite. 1,3-Dicyclohexylguanidinium acyclovir 5'-phosphoramidate (3.6 mmole) and methylenediphosphonic acid (10.8 mmole) are treated with 54 ml of freshly distilled o-chlorophenol; the mixture is cooled on ice and 36 ml of dry pyridine is added. This resulting solution is allowed to stand at RT with occasional shaking for 48 hr when 300 ml of water is added while cooling in ice. The solution is extracted six times with ether (850 ml total). The aqueous solution is adjusted to pH 2 with 1 N HCl and then treated with 30 g of acid-washed charcoal (Norit A) and stirred for 30 min; then the charcoal is collected by filtration and washed exhaustively with water (5 l total vol). The acyclovir derivative is eluted with 50% aqueous ethanol-5% concentrated ammonium hydroxide (3 l total) and the eluate is concentrated to a 400 ml volume by evaporation at 35° C. The concentrated eluate is applied to a 2.7 cm×31 cm column of Dowex-2™ (chloride; 8% cross linking) and eluted with a linear gradient made from mixing 2 l of 0.003 N HCl (in the mixing vessel) and 2 l of 0.003 N HCl plus 0.45 N LiCl (in the reservoir); 10 ml fractions are collected and fractions containing the acyclovir methylenediphosphonate are identified using paper chromatography or ultraviolet absorbance using methods well known in the art. The acyclovir methylenediphosphonate containing fraction is neutralized with 1 N LiOH and concentrated by evaporation at 30° C.; the concentrated solution is treated with 250 ml of acetone-10% methanol to precipitate a solid which is separated by centrifugation and washed with the acetone-10% methanol mixture until no chloride is detected in the washes. The Li-salt of acyclovir methylenediphosphonate can be further purified by dissolving the salt in 100 ml of water adjusted to pH 8 with LiOH and chromatographing the solution through a Dowex-2™ column as described above using a gradient made from 1.5 l of 0.003 N HCl in the mixing chamber and 1.5 l of 0.003 N HCl plus 0.45 N LiCl in the reservoir and treating the eluate as described above followed by dissolving the precipitate in 6 ml water and precipitating it with 40 ml of methanol. The final precipitate is dissolved in 15 ml of water and lyophilized to produce a powder of tetralithium acyclovir methylenediphosphonate.

Using Method 2, methylenediphosphonic acid (11.4 mmole) and acyclovir monophosphate (2.6 mmol) are dissolved in pyridine (30 ml) and water (4 ml) to produce a two-phase mixture to which DCC is added at RT with vigorous stirring in three aliquots (29 mmole at the start of the reaction; 48 mmole after 4 hr; and 19 mmole after 12 hr). After 24 hr, the reaction is completed and precipitated dicyclohexylurea is filtered off and washed with water. The filtrate and washings are adjusted to a total volume of 150 ml with water and extracted five times with ether (300 ml total). The solution is adjusted to pH 8 and chromatographed on a 2.5 cm×17.5 cm column of Dowex-1™ (formate; 2% cross linking) column; the column is washed with 1.5 l of water to remove pyridine. Elution from the column is carried out using a gradient created by adding successively to a mixing chamber containing 500 ml water the following solutions: 4 N formic acid (500 ml), 4 N formic acid plus 0.1 M ammonium formate (500 ml), and 4 N formic acid plus 0.2 M ammonium formate (1500 ml) and collecting 15 ml fractions. The fractions containing 2CdATMDP (approximately in tubes 115–134) are identified using ultraviolet absorption using methods well known in the art. The combined fractions containing 2CdATMDP are lyophilized to a volume of about 200 ml and then treated with 7 g of acid-washed charcoal (Norit A) and stirred for 15 min; then the charcoal is collected by filtration and washed with water (800 ml total). The product is eluted with 50% aqueous ethanol-5% concentrated ammonium hydroxide (600 ml total) and the eluate is concentrated to a 200 ml volume by evaporation at 20° C., filtered to remove trace amounts of charcoal and lyophilized to powder. The powder is dissolved in 4 ml of water and the solution is treated with excess 1 M barium acetate; the resulting precipitate is collected by centrifugation, washed with water and dissolved in 0.1 N HBr at 0° C. The solution is adjusted to pH 6.5 with 1 N NaOH and the resulting precipitate is collected by centrifugation, washed with successively with 2×2 ml each of water, ethanol and ether. The sample is dried at RT over $P_2O_4$ for 12 hr to yield dibarium 2CdATMDP hydrate. Other nucleoside analog phosphomethylenediphosphonates of the invention are prepared similarly.

EXAMPLE 11

Absence of Antiviral Effect of Acyclovir Monophosphate in Acyclovir-Resistant TK Mutant Strains of HSV (DM.21)

Separate cultures of Wi-38 fibroblast cells infected with either wild type strains of herpes simplex virus (HSV) or a mutant strain of HSV (DM.21) were individually treated with acyclovir, or acyclovir monophosphate. The DM.21 mutant lacks the thymidine kinase enzyme which usually converts ACV to ACV-MP, and is therefore resistant to acyclovir. The results for HSV-1 are shown in FIG. 1, and those for HSV-DM.21 are shown in FIG. 2. An $IC_{50}$ is that concentration of antiviral agent which inhibits viral plaque formation 50%.

In wild type isolates and laboratory strains of herpes simplex virus (HSV-1), acyclovir and acyclovir monophosphate have $IC_{50}$s of 0.1 $\mu$M (FIG. 1). In contrast, both acyclovir and acyclovir monophosphate have $IC_{50}$s in excess of 100 $\mu$M against mutant HSV strains in this assay (FIG. 2).

Based on these results in vitro, one would not expect acyclovir monophosphate to exhibit significant activity when administered topically to animals infected with a thymidine kinase defective or other mutant strain of HSV.

EXAMPLE 12

Antiviral Effect of Acyclovir Phosphate Esters in Mice Infected with Acyclovir-Resistant Strains of HSV Mice of the HRS/J type were infected cutaneously using the snout scarification method as described by Ellis, M. et al., *Antimicrobial Agents and Chemotherapy* 33(3):304–310 (1989). Briefly, groups of 10 mice, under light ether anesthesia, were inoculated on the snout by scarification with a 25-gauge needle, followed by 10 seconds of rubbing with a cotton-tipped applicator soaked in diluted virus. The virus used for infection was a TK-deficient strain, referred to in Ellis, M. et al. ($TK^D$). Three hours post-infection, the animals were treated topically, 3 times daily, for 4 days, with formulations of acyclovir or acyclovir phosphates, in a aqueous cream (AC), according to the Ellis reference cited above.

The results are presented in FIG. 3. A formulation comprising 5 gm % acyclovir was active. In contrast, a formulation comprising 5 gm % of a mixture of 80% acyclovir monophosphate together with 20% other acyclovir phosphate esters (acyclovir diphosphate and acyclovir diphosphate glycerol) showed superior activity, with only a few mice developing herpetic lesions. All lesions were healed by day 8 in all groups.

The above procedure was repeated, with treatment continuing for 5 days, using the TK-altered HSV-1 virus ($TK^A$, Ellis, above), a more virulent strain. Unlike the $TK^D$ virus, $TK^A$ is fatal in untreated mice. Treatment with 5 gm percent acyclovir reduced lesion scores moderately, with most animals surviving and improving substantially by day 14. With the same concentration of phosphate esters, however, there was a dramatic improvement in lesion scores, with all lesions resolved after 9 days, and all animals surviving, as shown in FIG. 4.

EXAMPLE 13

Antiviral Effect of Acyclovir Monophosphate in Mice Infected with an Acyclovir Resistant Wild Type HSV-1

The procedure of Example 12 was repeated using an acyclovir-sensitive, wild type HSV-1 and a formulation having only acyclovir monophosphate (ACV-MP) as the acyclovir derivative. Two creams were formulated, one having ACV-MP present in the aqueous cream at 14.5 millimoles/100 ml and the other having acyclovir present at 22.2 millimoles/100 ml (both 5 gm %, however, because of the addition of the phosphate group the number of moles of acyclovir present in the monophosphate is reduced relative to neat acyclovir).

Figure 5:
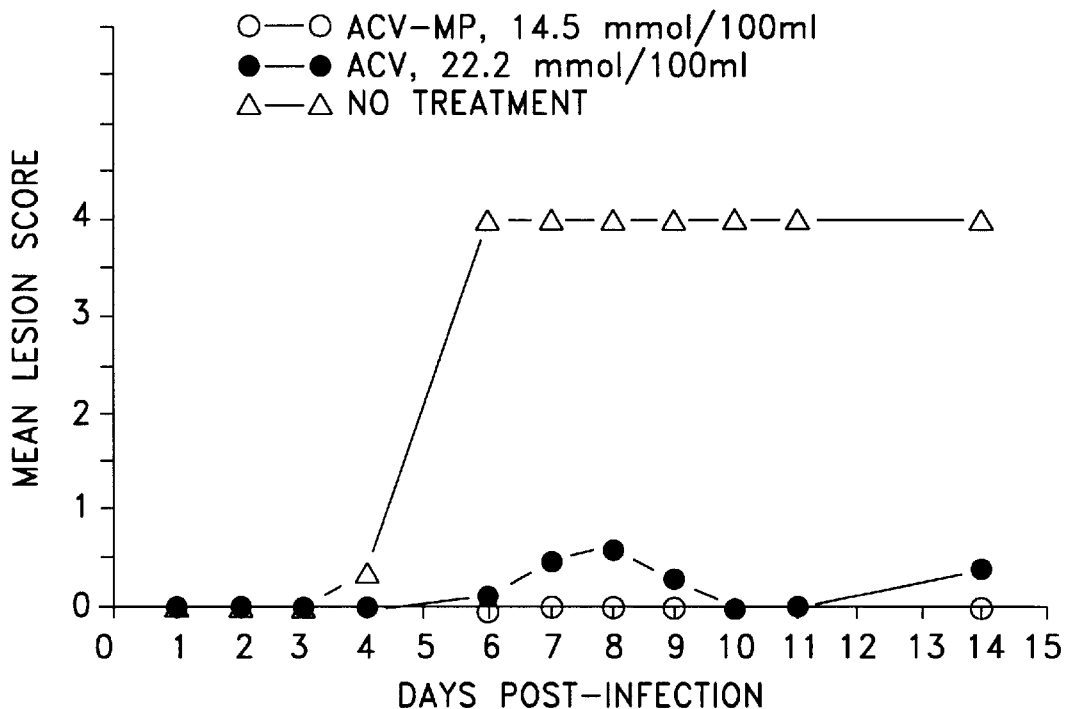
FIG. 5 illustrates the comparative effect of topical acyclovir and acyclovir monophosphate on acyclovir-resistant HSV-1 infections of the wild type in HRS/J mice.

Treatment was initiated 24 hours after infection and continued 4 times daily for four days. The ten untreated mice developed stage 4 lesions by the 5th day and all died by day 14 (FIG. 5). The acyclovir monophosphate-treated animals did not develop lesions and 10 of 10 animals survived (FIG. 5). In the acyclovir-treated group several animals developed mild lesions on days 7–9 which resolved; 9 of 10 ten animals survived.

This study shows that ACV-MP at a lower dosage (14.5 mmol/100 ml) was more effective than acyclovir (22.2 mmol/100 ml) in preventing lesions in wild type HSV-1 infection.

EXAMPLE 14

Antiviral Effect of Acyclovir Monophosphate in Mice Infected with an Acyclovir Resistant HSV-1

Figure 6:
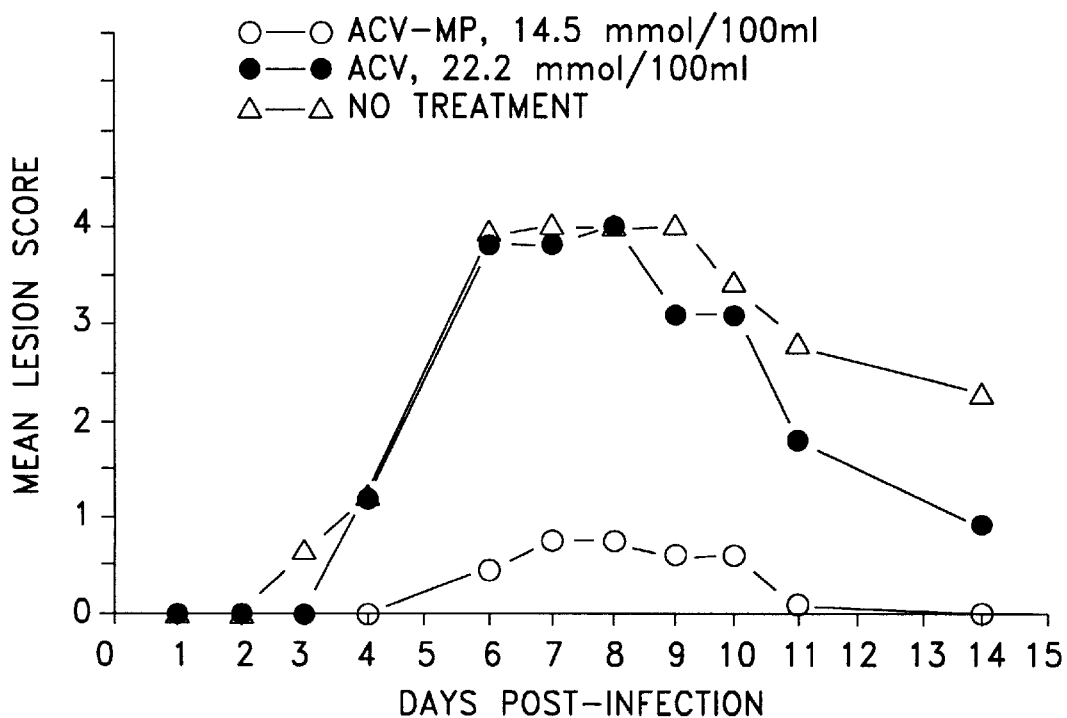
FIG. 6 illustrates the comparative effect of topical acyclovir and acyclovir monophosphate on acyclovir-resistant HSV-1 infections of the TK-altered type in HRS/J mice.

The procedure of Example 12 was repeated using a formulation having only acyclovir monophosphate (ACV-MP) as the acyclovir derivative. Treatment was begun 3 hours post-infection, with treatments occurring twice on the day of infection, and thereafter, three times a day through day 4. Referring now to FIG. 6, ACV-MP at 14.5 mmol/100 ml is clearly more effective than acyclovir at 22.2 mmol/100 ml in reducing lesion scores in animals infected with acyclovir-resistant (TK altered) HSV-1.

In the control and acyclovir-treated groups, 8 of 10 mice survived the 14 day experiment versus 10 of 10 surviving with acyclvoir monophosphate treatment.

EXAMPLE 15

Antiviral Effect of Acyclovir Monophosphate in Guinea Pigs Infected with an Acyclovir Resistant HSV-2

We tested acyclovir monophosphate (ACV-MP) in aqueous cream (AC) to determine if it was more effective than 5% Acyclovir in polyethylene glycol (ACV-PEG) for treatment of a primary genital herpes. In particular, we studied a genital herpes infection of guinea pigs caused by an ACV-resistant HSV-2. Additionally, we compared acyclovir treatments in two carrier systems: aqueous cream (AC) and polyethylene glycol (PEG). The experiments were placebo-controlled and uninfected animals were treated with each ACV preparation to assess skin and vaginal irritation.

Intravaginal inoculation of weanling guinea pigs with HSV-2 results in a primary genital infection is characterized by initial replication of virus in the vaginal tract followed by the development of external vesicular lesions. Virus titers peak on days one to three in the vaginal tract and gradually clear by days 7–10. The external genital lesions first appear on day four, peak lesion severity occurs on days 6–8, and the lesions generally heal by days 15–18.

Animals were inoculated with the HSV-2 strain 12247, which has an altered thymidine kinase and is resistant to in vitro treatment with ACV. Female Hartley guinea pigs (Charles River, Kingston, N.Y.) weighing 250–300 grams were first vaginally swabbed to remove vaginal secretions. After one hour, the animals were inoculated intravaginally with $2.4\times10^4$ plague forming units (pfu). Inoculation was accomplished by inserting a swab soaked with virus into the vaginal tract and rotating approximately six times.

Groups of 10 guinea pigs were treated both intravaginally and on the external genital skin with 0.1 ml (total of 0.2 ml per animal per treatment) of each preparation. Animals were treated three times daily for seven days beginning 24 hours post-viral inoculation. Three uninfected animals were treated with each preparation on the same schedule to assess local toxicity and irritation.

To determine the efficacy of the various treatments on HSV-2 replication in the vaginal tract, swabs of vaginal secretions were obtained during the primary infection on days 1, 3, 5, 7, and 10 after HSV-2 inoculation. The swabs were placed in tubes containing 2.0 ml of media, vortexed, and frozen at −70° C. until titrated for HSV. When all samples were collected, they were thawed, diluted serially, and HSV-2 titers were determined using rabbit kidney cells in a microtiter CPE assay.

We also measured the development and severity of external genital lesions to determine the efficacy of treatment. Severity of lesions was graded on a 0–5+ score. The presence or absence and severity of lesions was recorded for 19 days after viral inoculation. Infection rates, peak lesion scores, peak virus titers, areas under virus titer-day curves, and lesion score-day curves between PBS placebo-treated and PEG drug-treated or AC placebo-treated and AC drug-treated animals were compared using the Mann-Whitney U rank sum test. A p-value of 0.05 or less was considered significant.

The effect of topical treatment with ACV preparations on vaginal viral replication is shown in Table I. Only treatment with the ACV-MP preparations (5% ACV-MP-PEG or 5% ACV-MP-AC) significantly reduced the virus titer-day area under the curve (AUC) and mean peak virus titers.

TABLE I

EFFECT OF TREATMENT WITH ACYCLOVIR MONOPHOSPHATE ON VAGINAL VIRUS TITERS OF GUINEA PIGS INOCULATED INTRAVAGINALLY WITH AN ACYCLOVIR RESISTANT HSV-2

| Treatment$_A$ | # Virus Positive/# Inoculated | Virus Titer-Day Area Under Curve | P-Value | Mean Peak Virus Titer | P-Value |
|---|---|---|---|---|---|
| Placebo-PBS | 10/10 | 31.6 | — | 5.0 | — |
| Placebo-AC | 10/10 | 34.6 | NS$^B$ | 5.1 | NS |
| ACV-PEG | 10/10 | 33.4 | NS | 5.2 | NS |
| ACV-AC | 10/10 | 27.9 | NS | 4.6 | NS |
| ACV-MP-PEG | 6/10 | 3.4 | <0.001 | 2.0 | <0.001 |
| ACV-MP-AC | 9/10 | 14.5 | 0.001 | 3.7 | <0.05 |

A. Topical and intravaginal treatment was initiated 24 hours after viral inoculation and was continued three times daily for 7 days. Acyclovir content on a molar basis was lower in the tests conducted with acyclovir monophosphate (14.5 mmol/100 ml) versus those conducted with the neat acyclovir (22.2 mmol/100 ml).
B. NS = Not Statistically Significant when compared to the appropriate placebo-treated group.

The effect of topical treatment with ACV preparations on lesion development is depicted in Table II. Both ACV and ACV-MP preparations significantly altered the lesion score-day AUC when compared to the appropriate placebo-treated group. However, only therapy with 5% ACV-MP-PEG significantly reduced mean peak lesion scores.

TABLE II

EFFECT OF TREATMENT WITH ACYCLOVIR MONOPHOSPHATE ON EXTERNAL LESION DEVELOPMENT IN AN ACYCLOVIR RESISTANT GENITAL HSV-2 INFECTION OF GUINEA PIGS

| Treatment$_A$ | Lesion Score-Day Area Under Curve | P-Value | Mean Peak Lesion Score | P-Value |
|---|---|---|---|---|
| Placebo-PBS | 28.3 | — | 3.0 | — |
| Placebo-AC | 34.2 | NS$^A$ | 3.5 | NS |
| ACV-PEG | 9.5 | 0.001 | 1.8 | NS |
| ACV-AC | 19.3 | 0.01 | 2.5 | NS |
| ACV-MP-PEG | 1.7 | <0.001 | 0.7 | <0.001 |
| ACV-MP-AC | 23.4 | <0.05 | 2.3 | NS |

A. Topical and intravaginal treatment was initiated 24 hours after viral inoculation and was continued three times daily for 7 days. Acyclovir content on a molar basis was lower in the tests conducted with acyclovir monophosphate (14.5 mmol/ml) versus those conducted with the neat acyclovir (22.2 mmol/100 ml).
B. NS = Not Statistically Significant when compared to the appropriate placebo-treated group.

In the guinea pig model of an ACV-resistant HSV-2 genital herpes infection, only ACV-MP significantly reduced vaginal viral replication. Also, the ACV-MP-PEG treated group had the lowest virus titer-day and mean peak titer values. While both ACV-MP and ACV altered lesion development, the drugs in PEG had lower scores than those in AC. Additionally, animals receiving ACV-MP-PEG had the lowest lesion score-day and mean peak lesion scores.

Moreover, throughout the study, there were no signs of any irritation of the genital area or any other toxicity in uninfected ACV preparation-treated animals.

These results demonstrate the strong activity of acyclovir monophosphate in treating HSV-2 genital herpes. Further, it is interesting to note that polyethylene glycol dispersed acyclovir monophosphate showed the best efficacy in treating lesions.

EXAMPLE 16

Activity of Acyclovir Diphosphate

The procedure of Example 12 is repeated using a formulation having only acyclovir diphosphate (ACV-DP) as the acyclovir derivative. Efficacy superior to that of ACV alone is observed.

EXAMPLE 17

Activity of Acyclovir Monophosphate Glycerol

The procedure of Example 12 is repeated using a formulation having only acyclovir monophosphate glycerol (ACV-MP-G) as the acyclovir derivative. Efficacy superior to that of ACV alone is observed.

EXAMPLE 18

Activity of Acyclovir Diphosphate Glycerol

The procedure of Example 12 is repeated using a formulation having only acyclovir diphosphate glycerol (ACV-DP-glycerol) as the acyclovir derivative. Efficacy superior to that of ACV alone is observed.

EXAMPLE 19

Activity of Acyclovir Monophosphate Morpholidate

The procedure of Example 12 is repeated using a formulation having only acyclovir monophosphate morpholidate (ACV-MP-morpholidate) as the acyclovir derivative. Efficacy superior to that of ACV alone is observed.

EXAMPLE 20

Activity of Acyclovir Monophosphate Isopropylidene Glycerol

The procedure of Example 12 is repeated using a formulation having only acyclovir monophosphate isopropylidene glycerol (ACV-MP-isoP-G) as the acyclovir derivative. Efficacy superior to that of ACV alone is observed.

EXAMPLE 21

Activity of Acyclovir Diphosphate Isopropylidene Glycerol

The procedure of Example 12 is repeated using a formulation having only acyclovir diphosphate isopropylidene glycerol (ACV-DP-isoP-G) as the acyclovir derivative. Efficacy superior to that of ACV alone is observed.

EXAMPLE 22

Activity of Acyclovir-Phosphomethylenediphosphonate and Acyclovirtriphosphate

The procedure of Example 12 is repeated using a formulation having only ACV-Phosphomethylenediphosphonate and Acyclovirtriphosphate, independently, as the acyclovir derivative. Efficacy superior to that of ACV alone is observed.

EXAMPLE 23

Solubility of Acyclovir Monophosphate and Salts

Various salts of acyclovir monophosphate were tested for solubility as follows:

Two ml of distilled water was placed in each of three 10 ml beakers, each beaker having magnetic stirring bars. In each individual flask, an acyclovir monophosphate salt, selected from potassium, sodium, sodium/ammonium, and H$^+$ (free acid), was added until a saturated solution was formed. Each saturated salt solution was gravity filtered. The acyclovir monophosphate sodium/ammonium and free acid salt solutions were filtered through Whatman No. 4 filter paper and gave clear solutions. The potassium and sodium salt solutions were filtered through Whatman No. 1 filter paper and each gave slightly opalescent solutions.

One ml of each of the saturated salt solutions were transferred by pipette to preweighed round bottom flasks, and the solutions were allowed to dry. After all of the liquid had evaporated, the round bottom flasks were reweighed and the number of milligrams of acyclovir monophosphate salt present per milliliter was easily found.

The following Table sets forth the solubility of the various salts prepared as described above relative to acyclovir:

TABLE III

| Salt | Solubility as Compared to Acyclovir |
| --- | --- |
| H$^+$ | 21X |
| K$^+$ | 85X |
| Na$^+$/NH$_4^+$ | 100X |
| Na$^+$ | 108X |

It will be appreciated in view of the results shown in Table III, that through formation of a salt of the acyclovir monophosphate, solubility can be dramatically enhanced. It is expected that other nucleoside monophosphates will exhibit similarly enhanced solubility. In this manner, it is possible to formulate topical compositions containing large quantities of acyclovir monophosphate because of the enhanced solubility of the salts.

There will be various modifications, improvements, and applications of the disclosed invention that will be apparent to those skilled in the art, and the present application is intended to cover such embodiments. Although the present invention has been described in the context of certain preferred embodiments, it is intended that the full scope of the disclosure be measured only by reference to the following claims.

What is claimed is:

1. A pharmaceutical composition, comprising an effective concentration of an anti-herpes nucleoside analogue phosphate ester or mixtures or salts thereof, in a pharmaceutical carrier suitable for topical use wherein said nucleoside analogue phosphate ester is selected from the group consisting of nucleoside analogue phosphorothioates, nucleoside analogue phosphoamidates, and nucleoside analogue phosphofluoridates.

2. A pharmaceutical composition, comprising an effective concentration of an anti-herpes nucleoside analogue phosphate ester or mixtures or salts thereof, in a pharmaceutical carrier suitable for topical use wherein said nucleoside analogue phosphate ester is selected from the group consisting of 1,2-μ-methylene-nucleoside analogue diphosphates, 2,3-μ-methylene-nucleoside analogue triphosphates, 1,2-μ-thio-nucleoside analogue diphosphates, and 2,3-μ-thio-nucleoside analogue triphosphates.

3. The composition of claim 1 or 2 wherein said nucleoside analogue is acyclovir.

4. A pharmaceutical composition according to claim 1 or 2 comprising an effective concentration of an anti-herpes nucleoside analogue phosphate ester or mixtures or salts thereof, in a pharmaceutical carrier suitable for topical use wherein said nucleoside analogue phosphate ester is acyclovir triphosphate.

5. A pharmaceutical composition according to claim 1 or 2 comprising an effective concentration of an anti-herpes nucleoside analogue phosphate ester or mixtures or salts thereof, in a pharmaceutical carrier suitable for topical use, wherein said anti-herpes nucleoside analogue is selected from the group consisting of 1-beta-D-arabinofuranosyl-E-5-(2-bromovinyl)uracil;

2'-fluorocarbocyclic-2'-deoxyguanosine;

6'-fluorocarbocyclic-2'-deoxyguanosine;

1-(beta-D-arabinofuranosyl)-5(E)-(2-iodovinyl)uracil;

{(1r-1α, 2β, 3α)-2-amino-9-(2,3-bis(hydroxymethyl)cyclobutyl)-6H-purin-6-one} Lobucavir;

9H-purin-2-amine, 9-((2-(1-methylethoxy)-1-((1-methylethoxy)methyl)ethoxy)methyl)-(9CI);

trifluorothymidine;

9-[(1,3-dihydroxy-2-propoxy)methyl]guanine (ganciclovir);

5-ethyl-2'-deoxyuridine;

E-5-(2-bromovinyl)-2'-deoxyuridine;

5-(2-chloroethyl)-2'-deoxyuridine;

buciclovir;

6-deoxyacyclovir;

9-(4-hydroxy-3-hydroxymethylbut-1-yl)guanine;

E-5-(2-iodovinyl)-2'-deoxyuridine;

5-vinyl-1-beta-D-arabinofuranosyluracil;

1-beta-D-arabinofuranosylthymine;

2'-nor-2'deoxyguanosine;

1-beta-D-arabinofuranosyladenine.

6. The pharmaceutical composition of any one of claim 1, 2, 3, 4 or 5, wherein the nucleoside phosphate ester is in the form of a pharmaceutically acceptable salt.

7. The pharmaceutical composition of claim 6, wherein the salt is selected from the group consisting of sodium, potassium, ammonium, and hydrogen salts.

8. The pharmaceutical composition of claim 6, wherein the pharmaceutical carrier is selected from the group consisting of an aqueous cream and polyethylene glycol.

9. A pharmaceutical formulation, comprising an effective antiherpes concentration of an acyclovir triphosphate ester, in a pharmaceutical carrier suitable for topical use.

10. The formulation of claim 9 wherein the nucleoside analogue phosphate ester is in the form of a pharmaceutically acceptable salt.

11. The formulation of claim 9 wherein the salt is selected from the group consisting of sodium, potassium, ammonium, and hydrogen salts.

12. The formulation of claim 9 wherein the pharmaceutical carrier is selected from the group consisting of an aqueous cream and polyethylene glycol.

13. A method for treating a herpes virus infection that is resistant to acyclovir, comprising topically applying an effective amount of an acyclovir triphosphate ester, a pharmaceutically acceptable acyclovir triphosphate ester salt, or a mixture thereof, wherein the acyclovir triphosphate ester is selected from the group consisting of phosphorothioates, phosphoamidates, and phosphofluoridates, in a pharmaceutical carrier suitable for topical use, to the herpes virus-infected cutaneous or mucosal tissues of a herpes virus infected animal.

14. A method for treating a herpes virus infection that is resistant to acyclovir, comprising topically applying an effective amount of an acyclovir triphosphate ester, a pharmaceutically acceptable acyclovir triphosphate ester salt, or a mixture thereof, wherein the acyclovir triphosphate ester is selected from the group consisting of phosphorothioates, phosphoamidates, and phosphofluoridates, in a pharmaceutical carrier suitable for topical use, to the herpes virus-infected cutaneous or mucosal tissues of a herpes virus infected animal.

15. A method for treating a herpes labialis virus infection, comprising topically applying an effective amount of an acyclovir triphosphate ester, a pharmaceutically acceptable acyclovir triphosphate ester salt, or a mixture thereof, wherein the acyclovir triphosphate ester is selected from the group consisting of phosphorothioates, phosphoamidates, and phosphofluoridates, in a pharmaceutical carrier suitable for topical use, to the herpes virus-infected cutaneous or mucosal tissues of the orofacial region of a herpes virus infected animal.

16. A method for treating a herpes virus infection that is resistant to acyclovir, comprising topically applying an effective amount of an anti-herpes nucleoside phosphate ester, a pharmaceutically acceptable anti-herpes nucleoside phosphate ester salt, or a mixture thereof, wherein the anti-herpes nucleoside phosphate ester is selected from the group consisting of phosphorothioates, phosphoamidates, and phosphofluoridates, in a pharmaceutical carrier suitable for topical use, to the herpes virus-infected cutaneous or mucosal tissues of a herpes virus infected animal.

17. A method for treating a herpes virus infection that is resistant to acyclovir, comprising topically applying an effective amount of an acyclovir phosphate ester, a pharmaceutically acceptable acyclovir phosphate ester salt, or a mixture thereof, wherein the acyclovir phosphate ester is selected from the group consisting of phosphorothioates, phosphoamidates, and phosphofluoridates, in a pharmaceutical carrier suitable for topical use, to the herpes virus-infected cutaneous or mucosal tissues of a herpes virus infected animal.

18. A method for treating a herpes labialis virus infection, comprising topically applying an effective amount of an acyclovir phosphate ester, a pharmaceutically acceptable acyclovir phosphate ester salt, or a mixture thereof, wherein the acyclovir phosphate ester is selected from the group consisting of phosphorothioates, phosphoamidates, and phosphofluoridates, in a pharmaceutical carrier suitable for topical use, to the herpes virus-infected cutaneous or mucosal tissues of the orofacial region of a herpes virus infected animal.

19. The method of any one of claims 13, 14, 15, 16, 17 or 18 wherein the phosphate ester is in the form of a pharmaceutically acceptable salt.

20. The method of any one of claims 13, 14, 15, 16, 17 or 18 wherein the pharmaceutically acceptable salt is selected from the group consisting of sodium, potassium and ammonium salts.

21. The method of any one of claims 13, 14, 15, 16, 17 or 18 wherein the pharmaceutically acceptable carrier comprises a vehicle selected from the group consisting of an aqueous cream and polyethylene glycol.

22. The method of any one of claims 13, 14, 15, 16, 17 or 18 wherein the animal is a human being.

23. The method of any one of claims 13, 14, 15, 16, 17 or 18 wherein the cutaneous or mucosal tissues are infected by herpes simplex, type 1 virus.

24. The method of any one of claims 13, 14, 15, 16, 17 or 18 wherein the cutaneous or mucosal tissues are infected by herpes simplex, type 2 virus.

25. The method of claim 16, 17 or 18 wherein the herpes virus infected tissues are in the orofacial region of the animal body.

26. The method of claim 16, 17 or 18 wherein the herpes virus infected tissues are in the genital region of the animal body.

27. A method for treating a herpes virus infection in which the herpes virus has developed a resistance to one or more antiviral compounds due to an alteration or defect in the viral gene coding for thymidine kinase, comprising applying an effective amount of an anti-herpes nucleoside phosphate ester, a pharmaceutically acceptable anti-herpes nucleoside phosphate ester salt, or a mixture thereof, wherein the anti-herpes nucleoside phosphate ester is selected from the group consisting of phosphorothioates, phosphoamidates, and phosphofluoridates, in a pharmaceutical carrier suitable for topical use, to the herpes virus infected cutaneous or mucosal tissues of an animal.

28. A method for treating a herpes virus infection in which the herpes virus has developed a resistance to one or more antiviral compounds due to an alteration or defect in the viral gene coding for thymidine kinase, comprising applying an effective amount of an acyclovir phosphate ester, a pharmaceutically acceptable acyclovir phosphate ester salt, or a mixture thereof, wherein the acyclovir phosphate ester is selected from the group consisting of phosphorothioates, phosphoamidates, and phosphofluoridates, in a pharmaceutical carrier suitable for topical use, to the herpes virus infected cutaneous or mucosal tissues of an animal.

29. The method of claim 27 or 28 wherein the animal is a human being.

30. The method of claim 27 or 28 wherein the phosphate ester is in the form of a pharmaceutically acceptable salt.

31. The method of claim 30, wherein the pharmaceutically acceptable salt is selected from the group consisting of sodium, potassium, and ammonium salts.

32. The method of claim 27 or 28 wherein the pharmaceutical carrier comprises a vehicle selected from the group consisting of an aqueous cream and polyethylene glycol.

33. The method of claim 27 or 28 wherein the cutaneous or mucosal tissues are infected by herpes simplex, type 1 virus.

34. The method of claim 27 or 28 wherein the cutaneous or mucosal tissues are infected by herpes simplex, type 2 virus.

35. The method of claim 27 or 28 wherein the herpes virus infected tissues are in the orofacial region of the animal body.

36. The method of claim 27 or 28 wherein the herpes virus infected tissues are in the genital region of the animal body.

37. The method of any one of claims 16, 17, 18, 27 or 28 wherein the anti-herpes nucleoside analogue phosphate ester is a phosphate ester, a pharmaceutically acceptable phosphate ester salt, or a mixture thereof, of a compound selected from the group consisting of phosphorothioate, phosphoamidate and phosphofluorate esters of:

1-beta-D-arabinofuranosyl-E-5-(2-bromovinyl)uracil;

2'-fluorocarbocyclic-2'-deoxyguanosine;

6'-fluorocarbocyclic-2'-deoxyguanosine;

1-(beta-D-arabinofuranosyl)-5(E)-(2-iodovinyl)uracil;

{1R-1α, 2β,3α)}-2-amino-9-{2,3-bis(hydroxymethyl) cyclobutyl}1,9-dihydro-6H-purin-6-one};

9H-purin-2-amine, 9-((2-(1-methylethoxy)-1-((1-methylethoxy)methyl)ethoxy)methyl)-(9CI);

trifluorothymidine;

9-[(1,3-dihydroxy-2-propoxy)methyl]guanine;

5-ethyl-2'-deoxyuridine;
E-5-(2-bromovinyl)-2'-deoxyuridine;
5-(2-chloroethyl)-2'-deoxyuridine;
buciclovir;
6-deoxyacyclovir;
9-(4-hydroxy-3-hydroxymethylbut-1-yl)guanine;
E-5-(2-iodovinyl)-2'-deoxyuridine;
5-vinyl-1-beta-D-arabinofuranosyluracil;
1-beta-D-arabinofuranosylthymine;
2'-nor-2'deoxyguanosine; and
1-beta-D-arabinofuranosyladenine;
and mixtures thereof, in a pharmaceutical carrier suitable for topical use, to the herpes virus-infected cutaneous or mucosal tissues of a herpes virus infected animal.

38. A method for treating a herpes virus infection that is resistant to acyclovir, comprising topically applying an effective amount of an anti-herpes nucleoside triphosphate ester, a pharmaceutically acceptable anti-herpes nucleoside triphosphate ester salt, or a mixture thereof, wherein the anti-herpes nucleoside triphosphate ester is selected from the group consisting of 1-beta-D-arabinofuranosyl-E-5-(2-bromovinyl)uracil;
2'-fluorocarbocyclic-2'-deoxyguanosine;
6'-fluorocarbocyclic-2'-deoxyguanosine;
1-(beta-D-arabinofuranosyl)-5(E)-(2-iodovinyl)uracil;
{1R-(1α,2β,3α)}-2-amino-9-{2,3-bis(hydroxymethyl) cyclobutyl}1,9-dihydro-6H-purin-6-one};
9H-purin-2-amine, 9-((2-(1-methylethoxy)-1-((1-methylethoxy)methyl)ethoxy)methyl)-(9CI);
trifluorothymidine;
9-[(1,3-dihydroxy-2-propoxy)methyl]guanine;
5-ethyl-2'-deoxyuridine;
E-5-(2-bromovinyl)-2'-deoxyuridine;
5-(2-chloroethyl)-2'-deoxyuridine;
buciclovir;
6-deoxyacyclovir;
9-(4-hydroxy-3-hydroxymethylbut-1-yl)guanine;
E-5-(2-iodovinyl)-2'-deoxyuridine;
5-vinyl-1-beta-D-arabinofuranosyluracil;
1-beta-D-arabinofuranosylthymine;
2'-nor-2'deoxyguanosine; and
1-beta-D-arabinofuranosyladenine;
and mixtures thereof, in a pharmaceutical carrier suitable for topical use, to the herpes virus-infected cutaneous or mucosal tissues of a herpes virus infected animal.

* * * * *